(12) United States Patent
Behling et al.

(10) Patent No.: US 12,108,738 B2
(45) Date of Patent: Oct. 8, 2024

(54) INSECT STORAGE AND RELEASE

(71) Applicant: Verily Life Sciences LLC, South San Francisco, CA (US)

(72) Inventors: Charles Behling, Brisbane, CA (US); Brian Wasson, Columbus, OH (US)

(73) Assignee: Verily Life Sciences LLC, South San Franciso, CA (US)

( * ) Notice: Subject to any disclaimer, the term of this patent is extended or adjusted under 35 U.S.C. 154(b) by 846 days.

(21) Appl. No.: 16/819,936

(22) Filed: Mar. 16, 2020

(65) Prior Publication Data

US 2020/0296920 A1   Sep. 24, 2020

Related U.S. Application Data

(60) Provisional application No. 62/925,328, filed on Oct. 24, 2019, provisional application No. 62/820,228, filed on Mar. 18, 2019.

(51) Int. Cl.
| | |
|---|---|
| *A01K 1/08* | (2006.01) |
| *A01K 1/03* | (2006.01) |
| *A01K 67/033* | (2006.01) |
| *B65D 75/36* | (2006.01) |

(52) U.S. Cl.
CPC ............... *A01K 1/08* (2013.01); *A01K 1/031* (2013.01); *A01K 67/033* (2013.01); *B65D 75/367* (2013.01)

(58) Field of Classification Search
CPC ........ A01K 1/08; A01K 1/031; A01K 67/033; B65D 75/367
See application file for complete search history.

(56) References Cited

U.S. PATENT DOCUMENTS

| | | | | |
|---|---|---|---|---|
| 3,345,974 | A | * 10/1967 | Phillips | A01K 67/033 119/51.01 |
| 4,212,267 | A | 7/1980 | Patterson | |
| 4,215,797 | A | 8/1980 | Chen | |
| 5,398,642 | A | * 3/1995 | Harwich | A01K 67/033 119/6.5 |
| 5,586,406 | A | * 12/1996 | Lin | A01K 97/04 43/56 |

(Continued)

FOREIGN PATENT DOCUMENTS

| | | |
|---|---|---|
| CA | 2510344 | 11/2006 |
| CH | 623539 | 6/1981 |

(Continued)

OTHER PUBLICATIONS

International Application No. PCT/US2020/023019, International Search Report and Written Opinion, mailed Jul. 29, 2020, 11 pages.

(Continued)

*Primary Examiner* — Monica L Perry
*Assistant Examiner* — Aaron M Rodziwicz
(74) *Attorney, Agent, or Firm* — Kilpatrick Townsend & Stockton LLP

(57) ABSTRACT

An insect storage and release device includes a rigid container used to store and transport insects. The insect storage and release device holds compressed insects or non-compressed insects. The insect storage and release device includes a removable enclosure and a reticulated foam. The reticulated foam provides compliance during packing of the insects.

12 Claims, 14 Drawing Sheets

(56) References Cited

U.S. PATENT DOCUMENTS

| | | | |
|---|---|---|---|
| 5,630,374 A * | 5/1997 | Cunningham | A01K 97/04 119/6.5 |
| 5,895,310 A * | 4/1999 | Otomo | A01K 67/033 449/20 |
| 6,129,051 A | 10/2000 | Jessie et al. | |
| 6,561,125 B1 | 5/2003 | Lohsomboon | |
| 6,926,152 B2 * | 8/2005 | Leung | B65D 25/04 446/72 |
| 6,971,513 B2 * | 12/2005 | Weinstein | B65D 11/02 206/321 |
| 7,174,847 B1 * | 2/2007 | Hulteen, III | A01K 63/003 43/132.1 |
| 7,444,957 B2 * | 11/2008 | Vadis | A01K 63/003 119/6.5 |
| 2004/0231230 A1 | 11/2004 | Wright | |
| 2008/0047494 A1 | 2/2008 | Vadis | |
| 2011/0067293 A1 | 3/2011 | Schneidmiller et al. | |
| 2013/0340319 A1 * | 12/2013 | AlAyedh | A01M 1/106 43/107 |
| 2015/0041593 A1 * | 2/2015 | Markov | B64D 1/08 244/137.1 |
| 2015/0210450 A1 | 7/2015 | Mercado et al. | |
| 2015/0253055 A1 | 9/2015 | Tsui | |
| 2020/0281164 A1 * | 9/2020 | Lepek | A01K 67/033 |

FOREIGN PATENT DOCUMENTS

| | | |
|---|---|---|
| CN | 204297380 | 4/2015 |
| CN | 107372366 A | 11/2017 |
| JP | 2004113061 A | 4/2004 |
| JP | 2007110969 A | 5/2007 |
| KR | 20090003665 U | 4/2009 |

OTHER PUBLICATIONS

International Application No. PCT/US2020/023019, Invitation to Pay Additional Fees and, Where Applicable, Protest Fee, mailed Jun. 3, 2020, 2 pages.

European Application No. 20774787.4 , "Intention to Grant", Dec. 8, 2022, 8 pages.

European Application No. 20774787.4 , Extended European Search Report, Mailed on Mar. 16, 2022, 8 pages.

Dominican Republic Application No. DOP2021-0187 , "Office Action", Dec. 5, 2022, 6 pages.

Singapore Application No. 11202109800X , "Written Opinion", Jan. 17, 2023, 10 pages.

Europe Appl. No. 23175036.5, Extended European Search Report, Jul. 28, 2023, 9 pages.

* cited by examiner

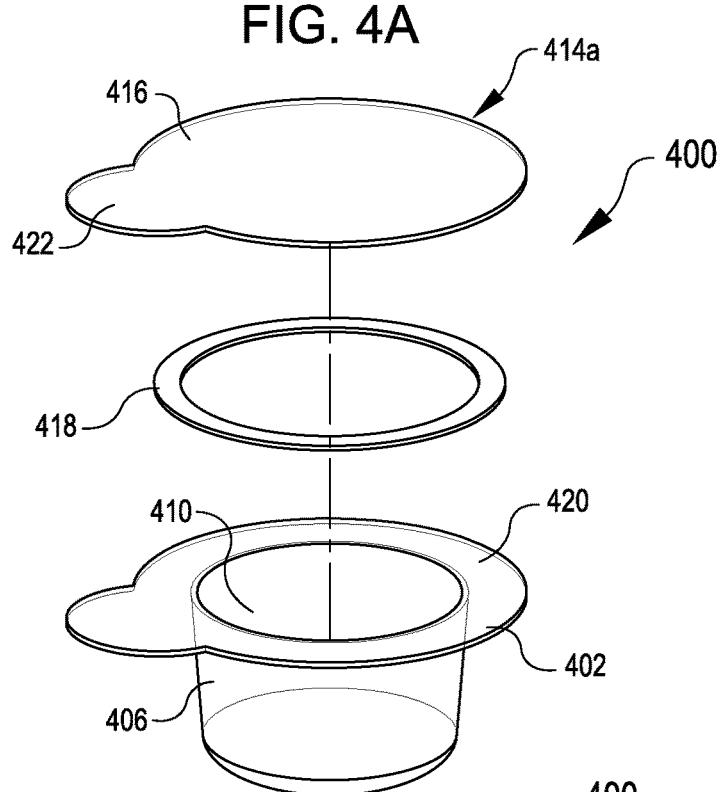
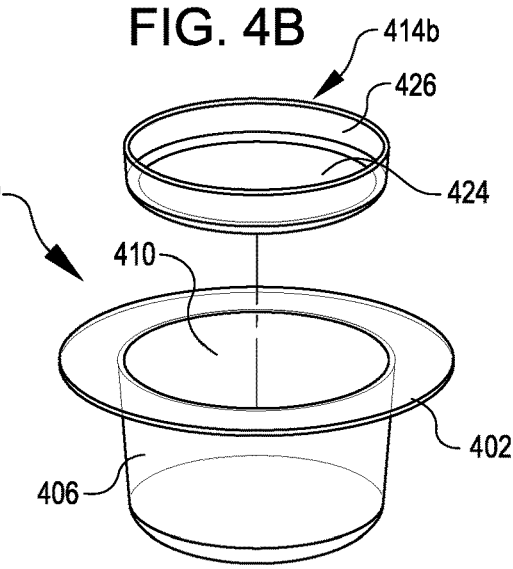
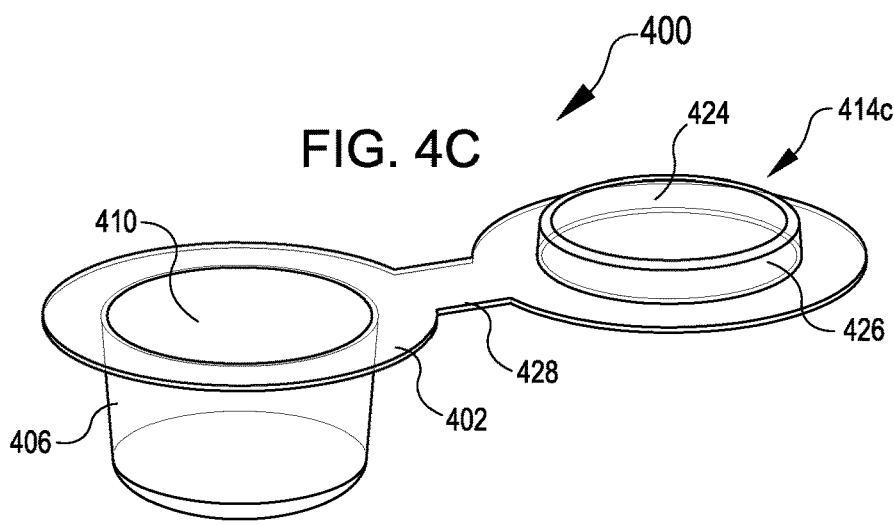

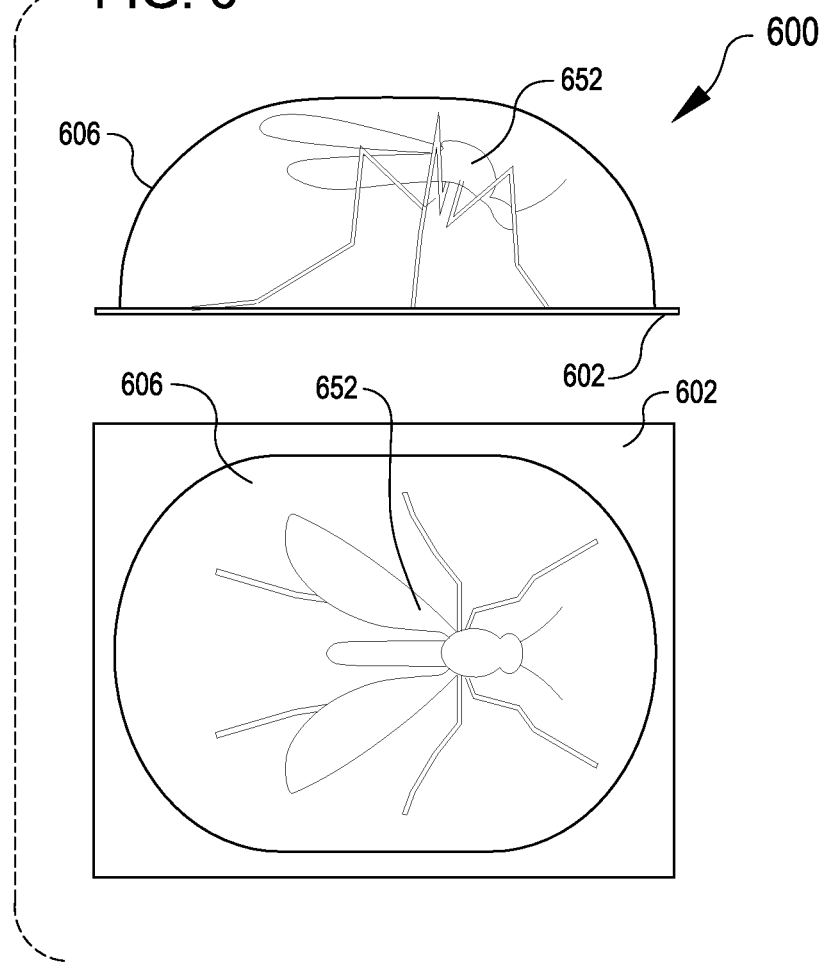

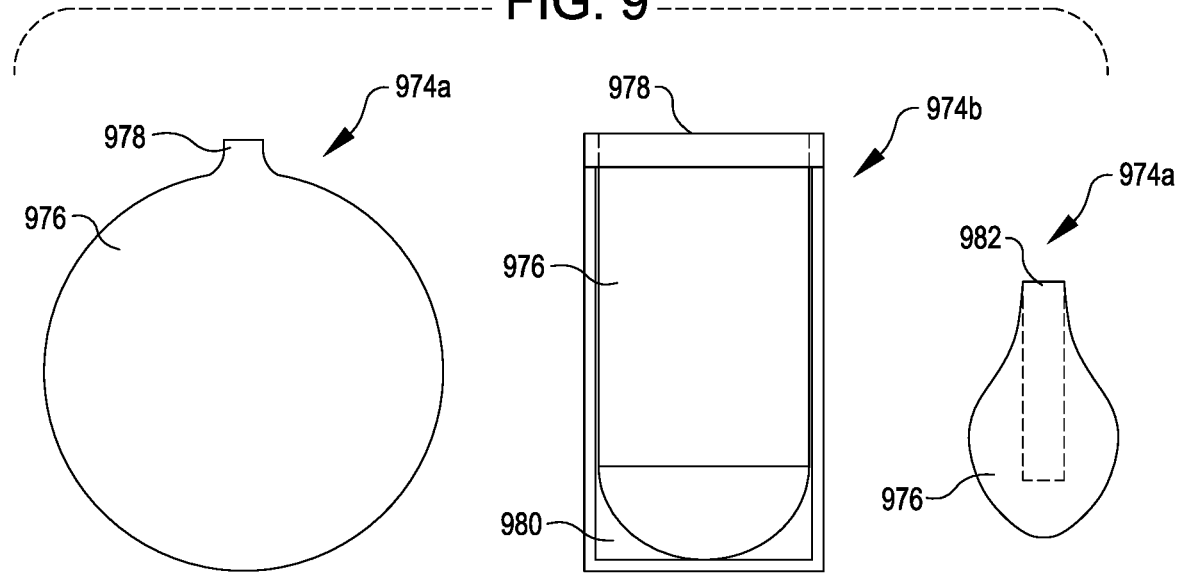
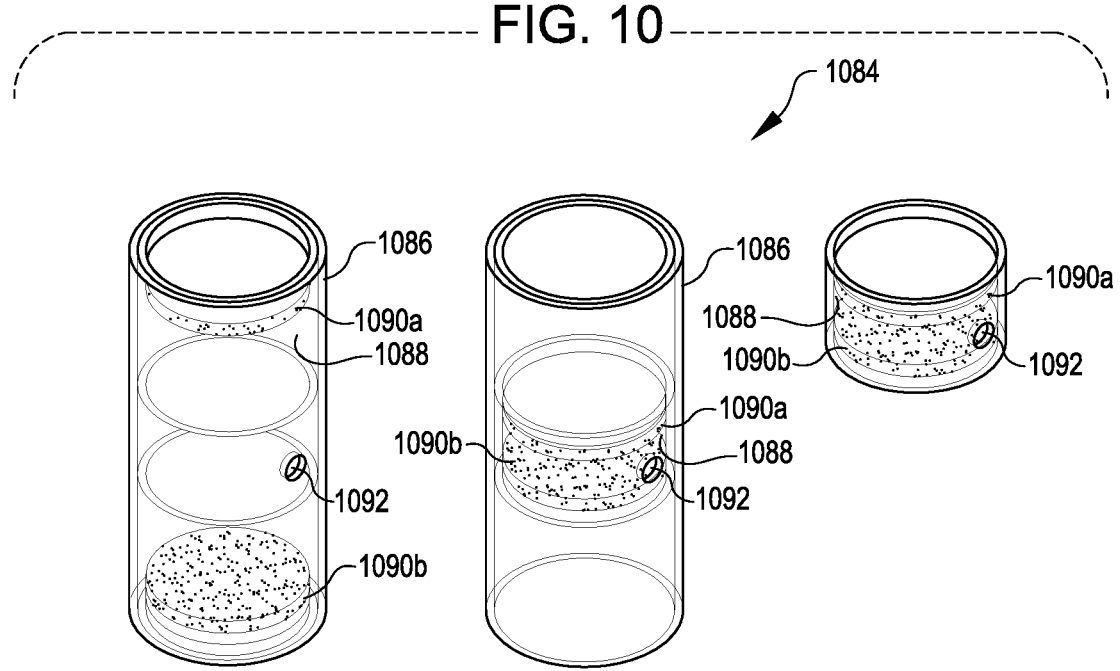

INSECT STORAGE AND RELEASE

CROSS-REFERENCE TO RELATED APPLICATIONS

This application claims priority to U.S. Provisional Patent Application No. 62/820,228, titled "Insect Storage and Release", filed Mar. 18, 2019, and U.S. Provisional Patent Application No. 62/925,328, titled "Insect Storage and Release", filed Oct. 24, 2019, the entireties of which are hereby incorporated by reference.

BACKGROUND

Insects, especially those reared in a laboratory, may require transportation between various stations within the laboratory and to different locations outside of the laboratory. Depending on the stage of development of the insects, different means of transportation may be appropriate.

BRIEF SUMMARY

Various examples are described relating to devices, systems, and methods for insect storage and release.

One general aspect includes an insect storage and release device, including: a bottom, a top flange, and a perimeter wall that connects the bottom and the top flange, where the perimeter wall and the bottom form a cylinder that defines a cylindrical interior volume for receiving a population of insects, and where an opening is formed in the top flange. The insect storage and release device also includes a population of insects disposed within the interior volume. The insect storage and release device also includes a lid sized and configured to enclose the opening and prevent the population of insects from exiting the cylinder.

Another general aspect includes a system, including: a bottom section including a plurality of insect sections, each insect section including an insect compartment, each insect compartment including at least one live insect. The system also includes a lid that extends over and encloses each insect compartment. The lid is configured for individual access to each insect compartment.

Another general aspect includes a method of compressing insects, including: loading an insect container into a retainer. The method of also includes adding a population of insects to an interior volume of a compression device. The method also includes adding a foam section to the interior volume of the compression device. The method also includes compressing the interior volume of the compression device and transferring the population of insects and the foam section to the insect container.

Another general aspect includes an insect rearing device, including: a pouch in which is formed a pocket. The insect rearing device also includes a first duct connected to a first side of the pocket and extending in a first direction. The first duct is configured to retain an aqueous solution, larvae insect food, and one or more insect larvae. The insect rearing device also includes a second duct connected to a second side of the pocket and extending in a second direction, the second duct configured to retain adult insect food.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 4A illustrates a perspective view of an insect storage and release device including a first lid configuration, according to at least one example.

FIG. 4B illustrates a perspective view of an insect storage and release device including a second lid configuration, according to at least one example.

FIG. 4C illustrates a perspective view of an insect storage and release device including a third lid configuration, according to at least one example.

FIG. 6 illustrates various views of an insect storage and release device, according to at least one example.

FIG. 9 illustrates side section views of insect loading and storage systems, according to various examples.

FIG. 10 illustrates perspective views of an insect loading and storage system, according to at least one example.

DETAILED DESCRIPTION

Figure 1:
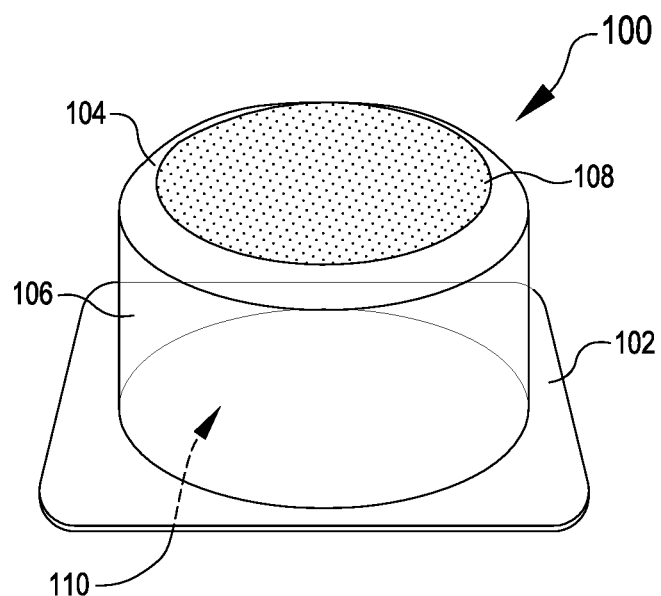
FIG. 1 illustrates a perspective view of an insect storage and release device, according to at least one example.

Examples are described herein in the context of storage of adult stage insects, and in particular adult stage mosquitoes. Those of ordinary skill in the art will realize that the following description is illustrative only and is not intended to be in any way limiting. For example, the techniques described herein can be used to store mosquitoes in other stages of development and/or other insects. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

As part of a sterile insect technique (SIT) program or otherwise, it is desirable to release known quantities of sterile insects into a target environment. The systems and devices described herein are used to load, store, and transport known quantities of such sterile insects in easy-to-use single-use or reusable containers. Each container may hold as few as one insect or can be scaled to hold hundreds, thousands, tens of thousands, or even more insects. To increase density, in some applications, insects are compressed as they are loaded into containers.

Sheets or rolls of containers, which may include multiple containers, may be produced, loaded, and sent for distribution. Using sheets or rolls of containers enables "dosing" selection in which set numbers of containers can be opened and released. The containers described herein may be shipped to end users for release. For example, a homeowner participating in a SIT program may receive, in the mail or otherwise, a package of containers including a set number of insects and instructions for releasing the insects (e.g., release one container per day for a week). The homeowner may be responsible for opening the containers and releasing the insects. For example, for a typical yard, about two containers of 1000 mosquitoes may be opened each week.

Turning now to a particular example, a single-use insect storage and release device includes a cup having a cylindrical shape, and a cap. The insect storage and release device is configured to hold a compressed quantity of insects within an interior volume of the cup. To load the insect storage and release device, the cup is placed into a retainer of a loading device with an opening of the cup facing up. A barrel of a syringe is loaded with a reticulated foam wafer that has a diameter about equal to a cross-sectional area of the opening. A quantity of insects is then loaded into the barrel. With the foam wafer and insects in the barrel, a structure supporting the barrel is used to align the barrel with the cup in the retainer. Once aligned, a plunger of the syringe is used to push the insects via the foam into the interior volume of the cup, thereby compressing the insects beneath the foam. Once foam has passed into the interior volume, loading concludes. The cap may then be placed on the cup to keep the insects and the foam from escaping the interior volume. The cap and/or the cup may include small perforations or slits to provide ventilation for the insects within the interior volume.

This illustrative example is given to introduce the reader to the general subject matter discussed herein and the disclosure is not limited to this example. The following sections describe various additional non-limiting examples of insect storage and release systems.

Turning now to the Figures, FIG. 1 illustrates a perspective view of an insect storage and release device 100, according to at least one example. The insect storage and release device 100 may be used to store various quantities of insects (e.g., adult mosquitoes) in a compressed or non-compressed state. The insect storage and release device 100 may be sufficiently rigid to enable transportation of the insects between various locations (e.g., from an insect factory to a field delivery location). The insect storage and release device 100 may be designed for single use. For example, after the insects have been loaded into the insect storage and release device 100, as described elsewhere herein, and transported to a delivery location, a lid on the insect storage and release device 100 may be removed to free the insects from the insect storage and release device 100. In some examples, the insect storage and release device 100 may be adapted for use in automated delivery systems. For example, the insect storage and release device 100 may be loaded into a blower system that, once the lid has been opened, removes the insects using an airstream.

The insect storage and release device 100, which is illustrated with a top portion resting on a surface, includes a top flange 102, a bottom 104, and a side wall 106 that together define an interior volume 110, which may be referred to as an insect compartment. The side wall 106 may be around 20 mm tall and the interior volume may have a diameter of around 20 mm. In some examples, the side wall may be greater than or less than 20 mm tall and the diameter may be greater than or less than 20 mm. The dimensions of the side wall and diameter may be selected based on a quantity of insects to store in the insect storage and release device 100 and a packing density for the insects (e.g., a quantity of insects per volume). In some examples, other factors, which may relate to packing density or otherwise, such as a mortality rate (e.g., a percentage of insects that die during packing and/or transport) may also be considered.

The insect storage and release device 100 has a cylindrical form factor, but other form factors such as rectangular, bulbous, and those corresponding to other shapes are also possible. The bottom 104 includes a perforated section 108. The perforated section 108 includes small slits, cuts, holes, or other perforations to enable air flow into and out of the interior volume 110. This allows air transfer between the interior volume 110 and outside the insect storage and release device 100. A lid such as one described with reference to later figures is used to seal an opening formed where the top flange 102 and an upper edge of side wall 106 intersect.

The illustrated insect storage and release device 100 is formed from a thermoformable plastic. However, other materials may be employed such as foil, paper, compostable products, rubbers, silicone/urethane, foam, 3D printed resin and filament, insect food (e.g., sucrose, bread, etc.). In some examples, the material used may be color coded to signify a characteristic such as volume of the container or quantity of insects held therein. The material may also be tinted (e.g., tinted plastic), UV protected (e.g., UV protected plastic), and have color-changing properties.

The insect storage and release device 100 may also be loaded with food (e.g., sugar water, sugar capsule, etc.). In some examples, the sugar water mixture is placed on the opposite side of the perforated section 108 and/or included in a foam wafer placed in the insect storage and release device 100.

In some examples, the insect storage and release device 100 is loaded directly from an insect sortation system. The insect sortation system may be configured to singulate and sort insects based on predefined characteristic (e.g., sex, species, size, etc.). Once singulated, the insects can be blown, driven, or otherwise loaded into the insect storage and release devices 100 from a singulation pathway of the insect sortation system. In some examples, insects from the singulation pathway are loaded into a holding chamber, and the insects are loaded from the holding chamber into the insect storage and release device 100. Whether using a singulation system or otherwise, the insect storage and release device 100 may be used to store insects of a particular characteristic (e.g., all male insects, all female insects, etc.).

Figure 2:
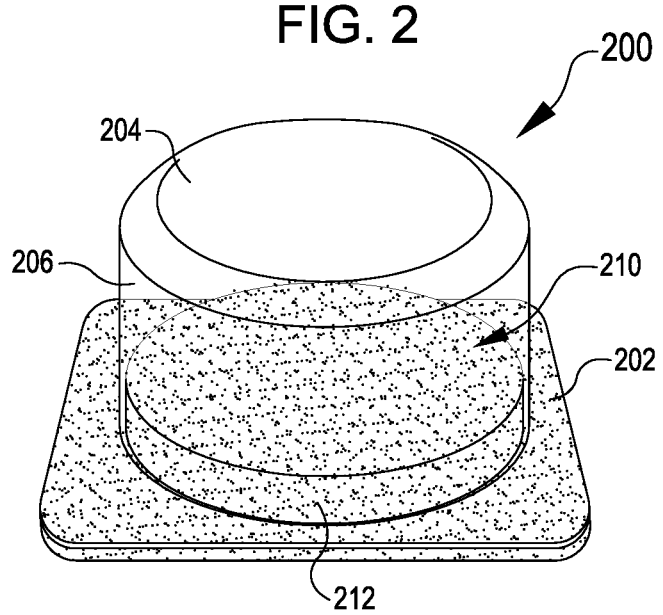
FIG. 2 illustrates a perspective view of an insect storage and release device, according to at least one example.

FIG. 2 illustrates a perspective view of an insect storage and release device 200, according to at least one example. The insect storage and release device 200 is an example of the insect storage and release device 100. The insect storage and release device 200 includes a foam section 212. A cylindrical portion of the foam section 212 extends into the interior volume 210, while a rectangular portion of the foam section 212 extends along the a top flange 202 of the insect storage and release device 200. The foam section 212, in this example, may form a lid for enclosing the interior volume 210. Unlike the insect storage and release device 100, the insect storage and release device 200 does not include a perforated section within bottom 204 or side wall 206. Instead, air flow is introduced into and out of the interior volume 210 via the foam section 212. In some examples, a lid is also used to seal the opening to the interior volume 210 (e.g., along the top flange 202). For example, the lid may be provided and formed of aluminum foil, plastic, or other material. In some examples, the lid may include a perforate section to enable airflow via the lid and the foam section 212. In some examples, the insect storage and release device 200 also includes a perforated section (e.g., when the lid forms an airtight seal).

The illustrated foam section 212 is a reticulated foam. However, any other open cell foam, silicone, plastic, or other material capable of being compressed similarly to such open-cell foams, etc. may be employed in place of the reticulated foam. The foam section 212 may be soaked in food, such as sugar water, for insects within the interior volume 210. In some examples, the interior volume 210 of the insect storage and release device 200 (and any other insect storage and release device described herein) is loaded with insect food such as a piece of fruit, sugar water, and any other such food. In other examples, food is supplied to insects within the insect storage and release device 200 (or within any other insect storage and release device) through openings in the bottom 204, the side wall 206, and/or the lid when these openings contact the food. For example, the insect storage and release device 200 (or any of the other insect storage and release devices described herein) may be placed on a towel, sponge, foam, or other absorbent object that has absorbed a liquid food (e.g., sugar water).

In some examples, a pressure-maintaining item is installed in between the foam section 212 and the lid. The pressure-maintaining item, which may include a variable force spring, a rigid pieces of material, such as a rigid plastic or metallic disk, a constant force spring, or other such item, may function to apply and/or maintain a constant pressure within the interior volume 210. For example, after the foam section 212 has been added to the interior volume 210, the pressure-maintaining item can be added, followed by the lid. The pressure-maintaining item may exert a force on the foam section 212 to ensure a constant pressure is maintained inside the interior volume 210.

Figure 3A:
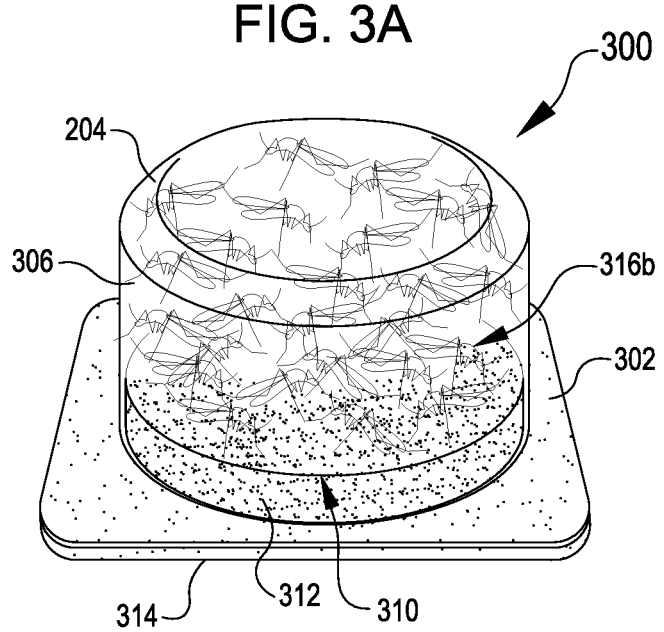
FIG. 3A illustrates a perspective view of an insect storage and release device including a first quantity of insects, according to at least one example.
Figure 3B:
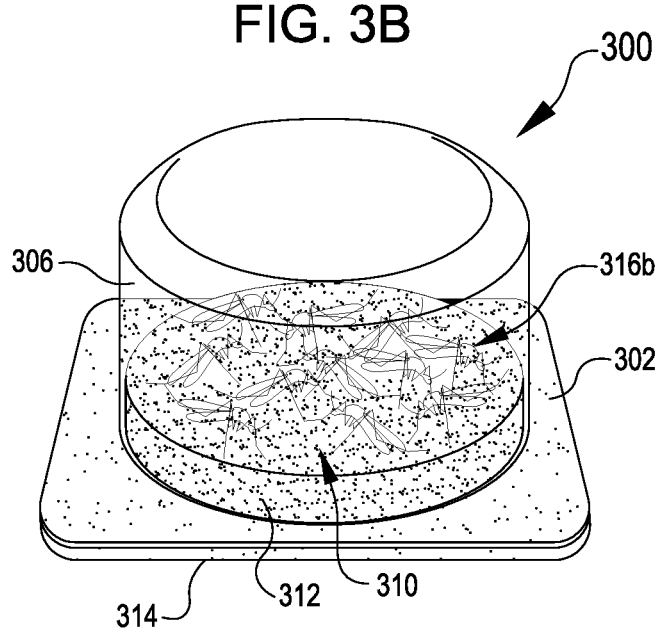
FIG. 3B illustrates a perspective view of an insect storage and release device including a second quantity of insects, according to at least one example.

FIGS. 3A and 3B illustrate a first perspective view and a second perspective view of an insect storage and release device 300, according to a few examples. In the insect storage and release device 300a of FIG. 3A, insects are stored in a compressed state. In the insect storage and release device 300b of FIG. 3B, insects are stored in an uncompressed state. The insect storage and release device 300 is an example of the insect storage and release devices 100 and 200.

The insect storage and release device 300 includes a lid 314 attached to a top flange 302 that encloses an interior volume 310. The insect storage and release device 300 also includes a foam section 312 located within the interior volume 310 between the lid 314 and a population of insects 316. The lid 314 includes an adhesive backing that is used to seal the lid to a top surface of the top flange 302. For example, the lid 314 may be formed from drywall tape (e.g., Tyvek® brand tape), peelable foil, perforated plastic, any other similar materials. In some examples, the lid 314 is formed from the foam section 312 or a second foam section. This example insect storage and release device 300 relies on air flow via the lid 314, i.e., the bottom 304 and the wall 306 are not perforated. As such, the lid 314 includes perforations and/or is formed from a material that allows breathability (e.g., air flow in and out of the interior volume 310). However, in some examples one or more of the lid, 314, the bottom 304, or the wall 306 may be perforated.

The insect storage and release device 300 in FIGS. 3A and 3B includes a population of insects 316a and 316b within the interior volume 310 of the insect storage and release device 300. The population of insects 316a in the insect storage and release device 300a have been compressed into the interior volume 310 using a compression device such as the one described with later figures. In some examples, the insects are compressed to between substantially 100-300 insects per milliliter, less than 100 insects per milliliter, or greater than 100 insects per milliliter. For example, the insect population 316a may include around 2000 adult insects (e.g., mosquitoes). In some examples, the insect population may be packed at a pressure of between substantially 0.5 PSI and 3 PSI. As described in more detail with respect to FIGS. 5A and 5B, this pressure may be measured based on a force applied to a packing actuator (e.g., at a handle 550 of a compression apparatus 534) given the surface area of a piston (e.g., a plunger 548) pushing against the population of insects (e.g., insects 516). In some examples, the pressure may be lower than 0.5 PSI and may be higher than 3 PSI. The population of insects 316b in the insect storage and release device 300b have not been compressed. As such, far fewer (e.g., around 25-50) insects make up the population of insects 316b. In some examples, as described elsewhere herein, a device is configured to store a single insect. In some examples, the insects 316 are compressed at least until some predefined packing pressure of the interior volume 310 is reached. To enable loading of the insects 316, the insects may be suppressed using a reduced temperature, a gas, or other such method to reduce physical activity and movement. In some examples, compressing of the interior volume 310 is performed at some predefined temperature (e.g., between substantially 0 degrees C. and 10 degrees C.) and/or while or after exposing the insects to a gas such as CO2 or Nitrogen to immobilize them. In some examples, the pre-defined temperature is less than 0 degrees C. and greater than 10 degrees C. The insect storage and release device 300 (or any other insect storage and release device described herein) may be shipped, transported, stored, or otherwise held at a constant holding temperature (e.g., between substantially 11 degrees C. and 15 degrees C.). In some examples, the constant holding temperature is less than 11 degrees C. and greater than 15 degrees C.

FIGS. 4A-4C respectively illustrate perspective views of an insect storage and release device 400 including various lid configurations 414a-414c, according to various examples. The insect storage and release device 400 is an example of the insect storage and release devices 100-300. The lids 414 may be reusable or disposable. In some examples, the lids 414 may be customized per application. The lids 414 may also include locking features and/or tamper-resistant features (e.g., foil that breaks when opened). For example, the lid 414 may include a locking feature that prevents children from unlocking the insect storage and release device 400 (e.g., child proof lock). In some examples, the locking feature may be unlocked only by one who has a key or by one who has a combination. This may be desirable to control the release of the insects only by those who are authorized as evidenced by key ownership. In some examples, the locking feature is a detent mechanism that includes a first portion connected to the lid and a second portion connected to the body. The detent mechanism may be configured to arrest rotation of the lid relative to the body. In some examples, the detent mechanism is mechanically manipulated in order to remove the lid from the body.

The insect storage and release device 400a illustrated in FIG. 4A includes the lid 414a. The lid 414a includes a planar piece 416 (e.g., a thin membrane of material) and an adhesive ring 418. The adhesive ring 418 seals the planar piece 416 to a top surface 420 of the top flange 402. The planar piece 416 also includes a tab 422 that corresponds to a similar shaped structure on the top flange 402. In some examples, the tab 422 is gripped by a user when opening the container to reveal the interior volume 410. In some examples, the adhesive ring 418 is formed as a planar sheet. In this example, a perimeter portion may adhere to the top surface 420 and the planar piece 416 and an inner portion may adhere to a foam section or other object disposed within the interior volume 410 and the planar piece 416. In this manner, removal of the planar piece 416 may also include removal of the foam section.

The insect storage and release device 400b illustrated in FIG. 4B includes the lid 414b. The lid 414b includes a lid bottom 424 and a lid wall 426 surrounding the lid bottom 424. To seal up the interior volume 410, the lid 414b is installed into the interior volume 410 via the opening located within the top flange 402. The lid 414b is held within the interior volume 410 by an interference fit between an exterior surface of the lid wall 426 and an interior surface of the side wall 406.

The insect storage and release device 400c illustrated in FIG. 4C includes the lid 414c. The lid 414c includes the lid bottom 424 and the lid wall 426 surrounding the lid bottom 424. The lid 414c also includes a connecting portion 428 that connects the top flange 402 and the lid bottom 424. The lid 414c functions similarly as described with reference to the lid 414b.

Figure 5A:
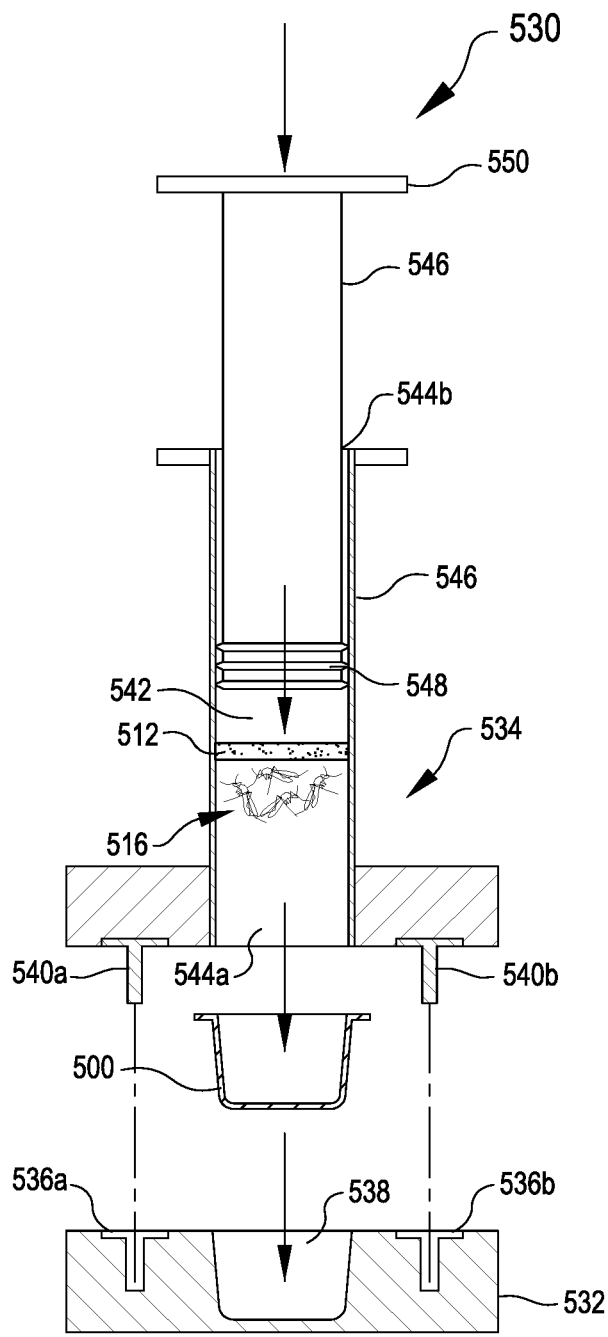
FIG. 5A illustrates a side sectional view of an insect compression device for loading insects into an insect storage and release device, according at least one example.
Figure 5B:
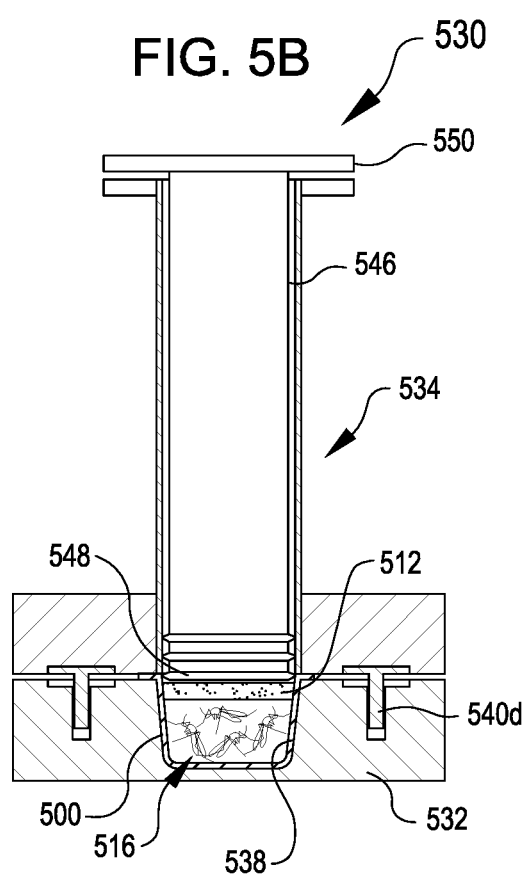
FIG. 5B illustrates a side sectional view of the insect compression device of FIG. 5A, according at least one example.

FIGS. 5A and 5B illustrate side sectional views of an example insect compression device 530 for loading insects into one of the insect storage and release devices described herein, according at least one example. The insect compression device 530 may be used to load insects into insect storage and release devices 500 (e.g., the insect storage and release devices 100-400), and, in some examples, this may include compressing the insects into the insect storage and release devices 500. For example, at least some of the insect populations 316 were loaded into their respective insect storage and release devices 300 using an insect compression device such as the insect compression device 530. The insect compression device 530 is used to load a single insect storage and release device, but it should be understood that multiple insect compression devices 530 may be held in any suitable combination and used to simultaneously load multiple insect storage and release devices with insects. For example, plurality of insect compression devices 530 may be arranged into a two-dimensional array of devices, which may be individually operated or may be aligned and actuated as a single system.

The insect compression device 530 includes a retainer block 532 and a compression apparatus 534. Generally, the retainer block 532 is configured to receive and retain an insect storage and release device 500 while the insect storage and release device 500 is being loaded with insects. The compression apparatus 534 is used to compress the insects into the insect storage and release device as it is retained by the retainer block 532.

Beginning with the retainer block 532, the retainer block 532 includes a set of alignment holes 536a-d surrounding a concave depression 538. The alignment holes 536 correspond to a set of alignment posts 540a-d of the compression apparatus 534, and are used to align the compression apparatus 534 with the retainer block 532. In the view depicted in FIGS. 5A and 5B, only two of the alignment holes 536 and two of the alignment posts 540 are illustrated. The other two may be located on opposite sides of their respective parts. In some examples, other alignment features may be employed or none may be used.

The concave depression 538 is configured to receive and retain the insect storage and release device 500. As such, the size and shape of the concave depression 538 may correspond to an exterior form factor of the insect storage and release device 500. In this example, the concave depression 538 may more or less has a cylindrical shape that corresponds to the cylindrical shape of the insect storage and release device 500 (e.g., such as the insect storage and release devices 100-400 described with respect to FIGS. 1-4). In other examples, the concave depression 538 may have a different size and shape. For example, the concave depression 538 may be bulbous to correspond to the insect storage containers described with respect to FIG. 6.

Turning now to the compression apparatus 534, the compression apparatus 534 includes a chamber 542 including a distal opening 544a and a proximate opening 544b, a plunger 546 including a distal end 548 and a handle 550, along with the alignment posts 540 introduced previously. The chamber 542 defines an interior volume extending between the two openings, 544a and 544b. The plunger 546 is configured to travel longitudinally (e.g., translate) within the interior volume of the chamber 542. To move the plunger 546, a user or a robotic device may exert a force on the handle 550 (e.g., either pushes to move the distal end 548 toward the distal opening 544a or pulls to move the distal end 548 toward the proximate opening 544b).

To operate the insect compression device 530, the compression apparatus 534 is separated from the retainer block 532. An insect storage and release device 500 is loaded into the concave depression 538 of the retainer block 532. The plunger 546 is pulled back within the chamber 542 to define a loading volume extending within the chamber 542 between the distal opening 544a and the distal end 548 (e.g., the distal end 548 is moved adjacent to the proximate opening 544b). Once the plunger 546 is in this position, a foam section 512 (e.g., the foam section 512 and/or a lid) is loaded into the chamber 542 via the distal opening 544a until it wrests against the distal end 548. A population of insects 516 may then be loaded into the chamber 542 via the distal opening 544a. In other examples, the distal end 548 is removed entirely from the chamber 542 and the population of insects 516 and the foam section 512 are loaded via the proximate opening 544b. Following these actions, the compression apparatus 534 and the retainer block 532 are brought into alignment via the alignment posts 540 and the alignment holes 536. Finally, the plunger 546 is moved through the interior volume of the chamber 542 such that the distal end 548 pushes the foam section 512 and the insects 516 toward the retainer block 532, which includes the insect storage and release device 500 loaded into the concave depression 538. In some examples, a packing pressure of substantially 0.5 PSI and 3 PSI may be applied to the insects 516 during packing. This pressure may depend on the force applied at the handle 550 given an area of the plunger 546. Once the insects 516 and the foam section 512 are within the insect storage and release device 500, the insect compression device 530 may be separated from the retainer block 532 and the loaded insect storage and release device 500 may be removed from the concave depression 538. In some examples, a lid may be loaded into the chamber 542 and translated within the interior volume as part of compressing the insects 516.

During loading of the insect storage and release device 500 using the insect compression device 530, the foam section 512 may be added to provide compliance during compression as well as to reduce damage to the insects 516 (e.g., the foam section 512 provides pressure on the insects 516, but does so without crushing the insects 516). The foam section 512 also allows the insects 516 to breathe.

In some examples, the insect compression device 530 includes any suitable compression cylinder/piston arrangement, cam shaft compression arrangement, or other suitable compression arrangement. This may enable automated loading. As described elsewhere herein, multiple insect compression devices 530 may be held together in an array of insect compression devices 530 to enable loading of multiple insect storage and release devices 500 simultaneously.

FIG. 6 illustrates various views of an insect storage and release device 600, according to at least one example. The insect storage and release device 600 (e.g., the insect storage and release devices 100-500) is configured to retain a single adult insect 652 such as a mosquito. The insect storage and release device 600 is shown as having a different form factor from the insect storage and release devices of FIGS. 1-4. However, the function and structure are similar. In particular, the insect storage and release device 600 includes a top flange 602 and a side wall 606. The side wall 606 has the form of a bulbous depression.

Figure 7:
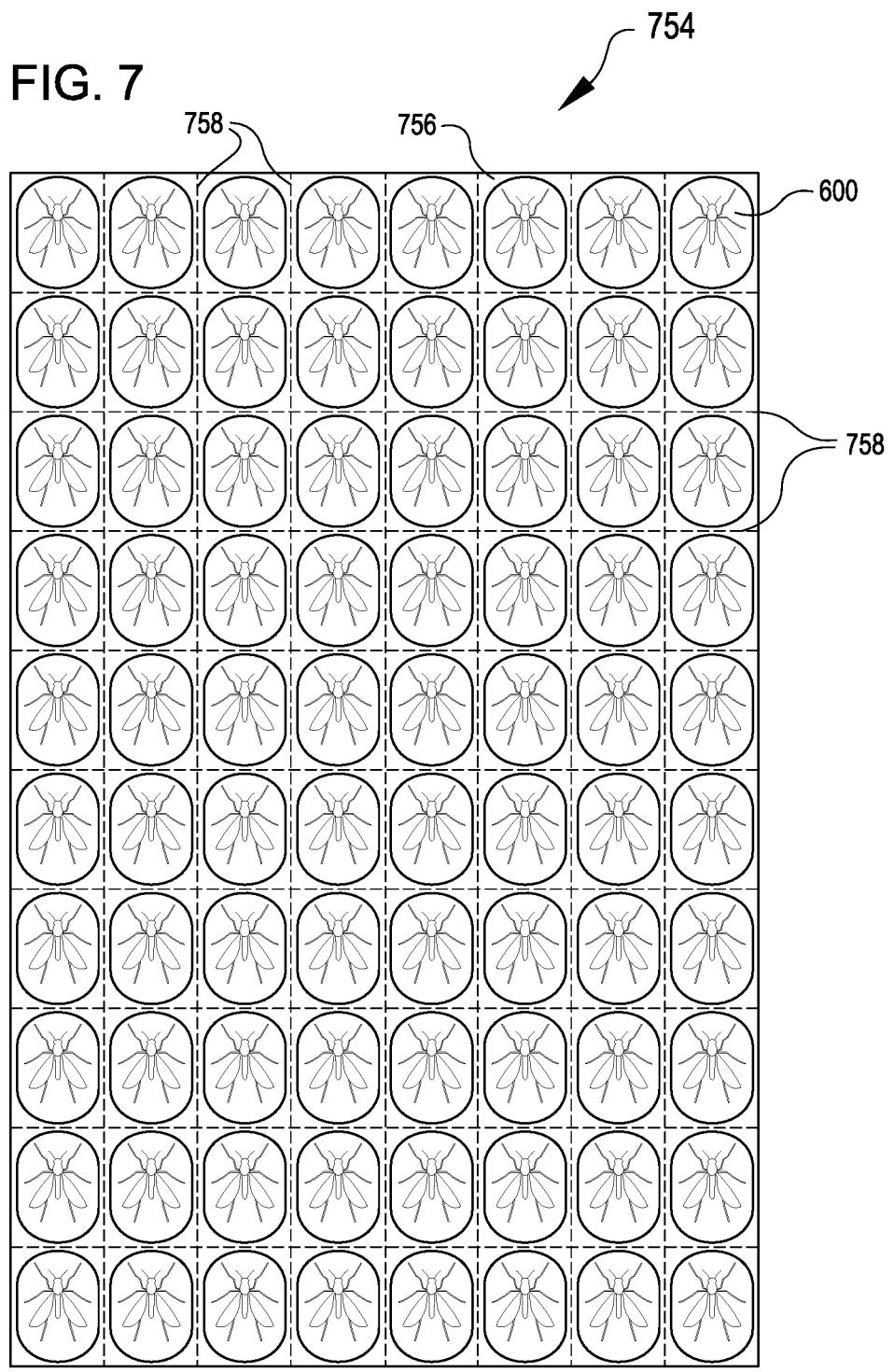
FIG. 7 illustrates various views of an insect storage system, according to at least one example.

In some examples, the insect storage and release device 600 (or any other insect storage and release device) may take the form factor of single-dispense blister packs such as those used to package medicine. For example, FIG. 7 illustrates an insect storage system 754 that includes a sheet 756 of the insect storage and release devices 600. The sheet 756 may include perforation lines 758 extending between the individual insect storage and release devices 600 (e.g., to define insect sections) such that each insect storage and release device 600 may be detached from the remaining insect storage and release devices 600 of the sheet 756. In some examples, the sheet 756 includes an adhesive back that can be removed to reveal the interior volume 610 of each insect storage and release device 600. In some examples, the sheet 756 includes a foil back that can be punctured to reveal the interior volume 610.

In some examples, the number of insects within each of the insect storage and release devices 600 on the sheet 756 may vary (e.g., 1 insect in one and 20 insects in another) or may be consistent (e.g., a full sheet of insect storage and release devices 600 each including 1 insect). In some examples, the sheet 756 is manufactured and loaded based on an order for a particular number of insects to be released at some dosage interval (e.g., 1 insect on a first day, 5 insects on a second day, 10 insects on a third day, etc.). The number of insect storage and release devices 600 in the sheet 756 may be defined as an array having any suitable number of rows and columns (e.g., 10×10, 1×1, 10×1, etc.).

Figure 8A:
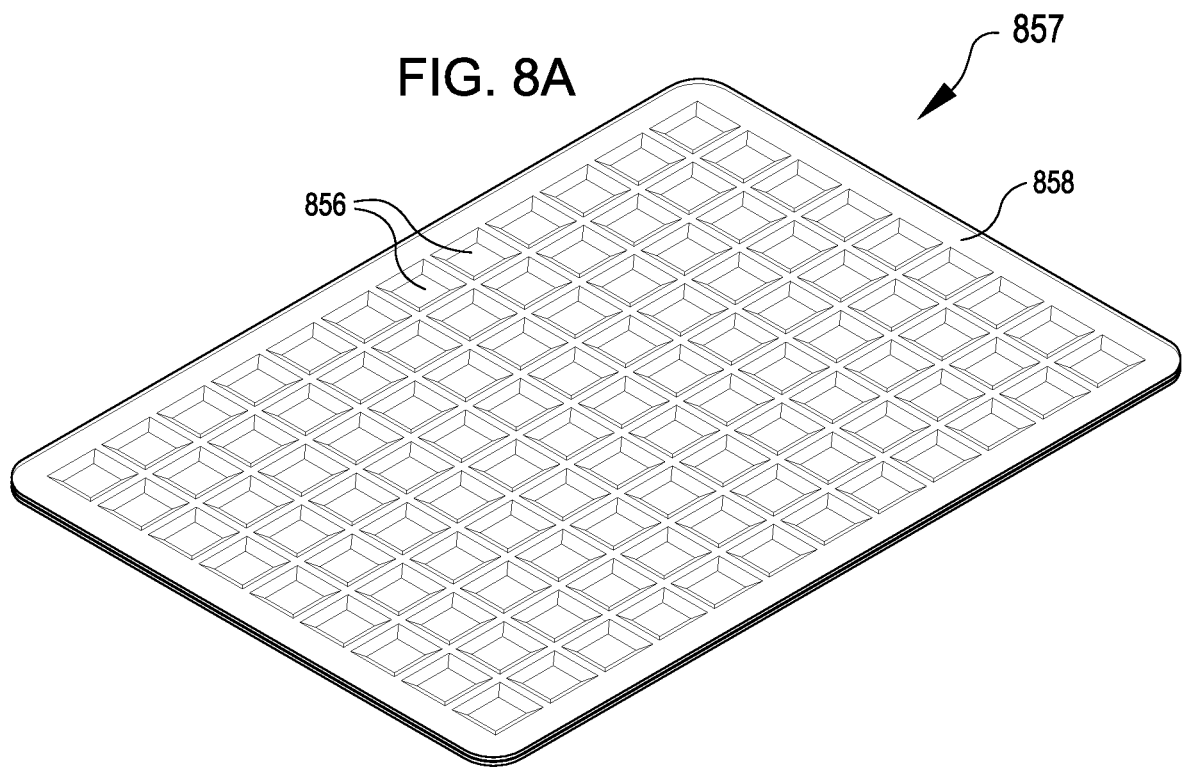
FIG. 8A illustrates a perspective view of an insect storage system, according to at least one example.

FIG. 8A illustrates a perspective view of an example insect storage system 854, according to at least on example. The insect storage system 854 is an example of the insect storage system 754. For example, the insect storage system 854 may be used store one or more insects. In some examples, the insect storage system 854 may include a bottom section 858 (e.g., a microplate) that includes a plurality of wells 856. In some examples, the bottom section 858 may be enclosed by a lid with flexible protrusions sized and configured to extend into the interior volumes of the wells 856 of the insect storage system 854. The insect storage system 854 may also be used to compress insects into the wells 856. In some examples, the insect storage system 854 may include perforations to allow air exchange and/or feeding.

Figure 8B:
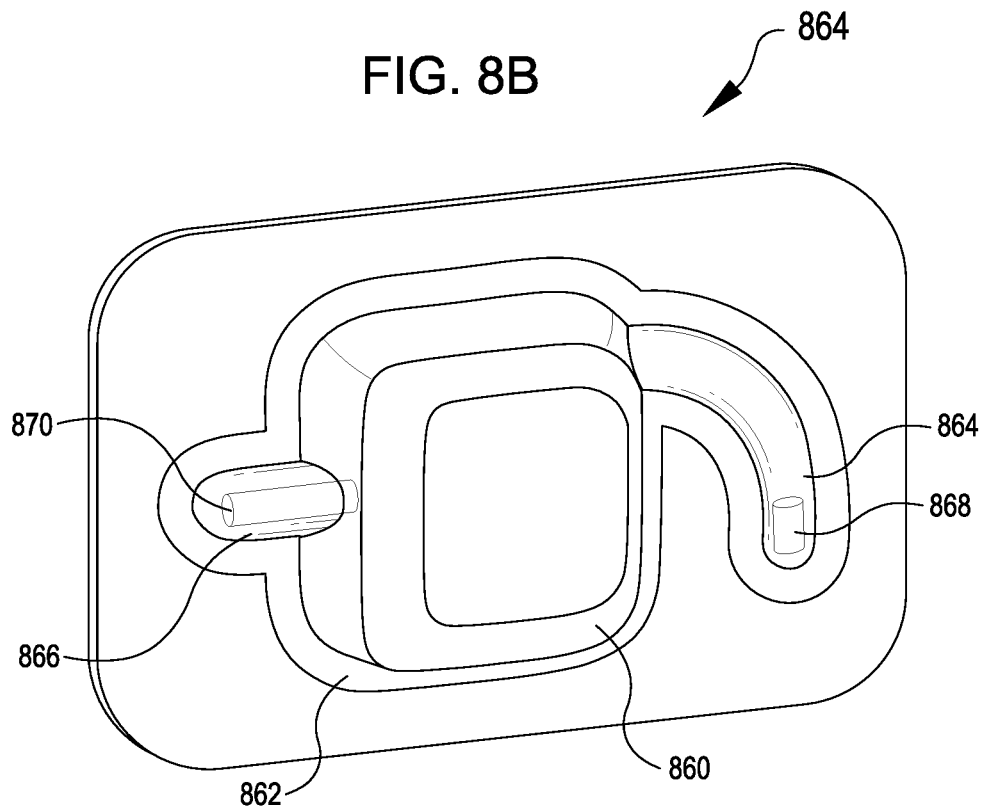
FIG. 8B illustrates a perspective view of an insect rearing and storage device, according to at least one example.

FIG. 8B illustrates a perspective view of an example insect rearing and storage device 857, according to at least one example. The insect rearing and storage device 857 is configured to house insects as they develop from a larva stage through the pupa stage and onto full adulthood. In some examples, the insect rearing and storage devices 857 are formed in a sheet such that many such devices 857 are included as part of one structure (e.g., a sheet of insect rearing and storage devices 857).

The insect rearing and storage device 857 includes a pouch 862 in which is formed a pocket 860. The pocket 860 forms a main chamber of the insect rearing and storage device 857. The insect rearing and storage device 857 also includes a first duct 864 connected to a first side of the pocket 860 and extending in a first direction and a second duct 866 connected to a second side of the pocket 860 and extending in a second direction. The first duct 864 is configured to retain an aqueous solution, larvae insect food 868, and one or more insect larvae. The second duct 866 is configured to retain adult insect food 870. The first duct 864 includes a proximate end that terminates at the pocket 860 and a distal end that terminates radially from the pocket 860. The second duct 866 includes a proximate end that terminates at the pocket 860 and a distal end that terminates laterally from the pocket 860.

In operation, one or more larvae and water are added to the first duct 864 while the insect rearing and storage device 857 is in the illustrated orientation. The larvae feed on the larvae insect food 868 and develop into pupae. Once this has occurred, the device 857 is rotated 90 degrees to the left. This causes the pupae to move through the first duct 864 and into the pocket 860, e.g., by gravity. Within the pocket 860, the pupae are suspended in water that drained from first duct 864 or other water while the develop into adults. Once adults, the insects can access the adult insect food 870 in the second duct 866. To provide air exchange for the insects, the insect rearing and storage device 857 includes a perforated section disposed at a suitable location of the pocket 860.

FIG. 9 illustrates side section views of insect loading and storage systems 974*a-c*, according to various examples. The insect loading and storage system 974 is used to compress insects into a balloon 976 using three different approaches. The system 974*a* includes the balloon 976 having an opening 978. The insects are loaded into the balloon 976 via the opening 978 with the balloon in an inflated state. Once within the balloon 976, the air can be evacuated from the balloon 976 to compress the insects.

The system 974*b* includes the balloon 976 with the opening 978 stretched over a container 980. The insects are loaded into the balloon 976 with the opening 978 stretched in this manner. Once within the balloon 976, the air can be evacuated from the balloon 976 to compress the insects.

The system 974*c* includes the balloon 976 and a loading straw 982. The loading straw 982 is inserted into an opening of the balloon 976. The insects are loaded into the balloon 976 via the loading straw 982. Once the insects have been loaded, the loading straw 982 may be removed from the balloon 976.

FIG. 10 illustrates perspective views of an insect loading and storage system 1084, according to at least one example. The insect loading and storage system 1084 is used to compress insects into a storage container 1086. The storage container 1086 includes an opening 1092 through which insects are loaded into an interior volume 1088. Once the insects have been loaded into the interior volume 1088, moveable walls 1090*a* and 1090*b* are moved to compress the interior volume 1088 and the insects found therein. Following this action, the moveable walls 1090*a* and 1090*b* may be moved relative to the opening 1092 to enable other insects to be loaded into other portions of the storage container 1086 formed by different moveable walls 1090.

In some examples, loading insects, whether using the insect loading and storage system 1084, the insect compression device 530, or any other loading device suitable for loading insects, may be include cooling, gassing using CO2 or other suitable gas, or other suitable techniques to immobilize the insects. For example, the temperature may be held between 9 degrees C. and 14 degrees C. In some examples, the insects are stored at this temperature, whether under compression or otherwise.

Figure 11:
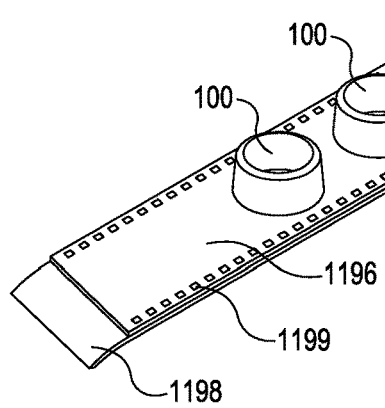
FIG. 11 illustrates a perspective view of an insect release system, according to at least one example.

FIG. 11 illustrates a perspective view of an example insect release system 1194, according to at least one example. The insect release system 1194 includes a plurality of insect storage and release devices 100 arranged into a top strip 1196, a bottom strip 1198, and a series of sprocket holes 1199. The insect release system 1194 takes the form factor of a film strip and can be loaded into an insect release device that is configured to open the insect storage and release devices 100 release insects disposed therein. For example, the insect release device may include one or more sprockets of other structure for indexing the insect release system 1194 between the insect storage and release devices 100. For example, such indexing can be achieved by the one or more sprockets engaging the sprocket holes 1199.

In some examples, the top strip 1196 includes an adhesive backing that connects the top strip 1196 to the bottom strip 1198. As the insect release system 1194 is indexed on an insect release device, the top strip 1196 may be separated from the bottom strip 1198 to release the insects held within the insect storage and release devices 100. Once opened, the insect release device may include a blower to blow the insects from the insect storage and release devices 100.

Figure 12:
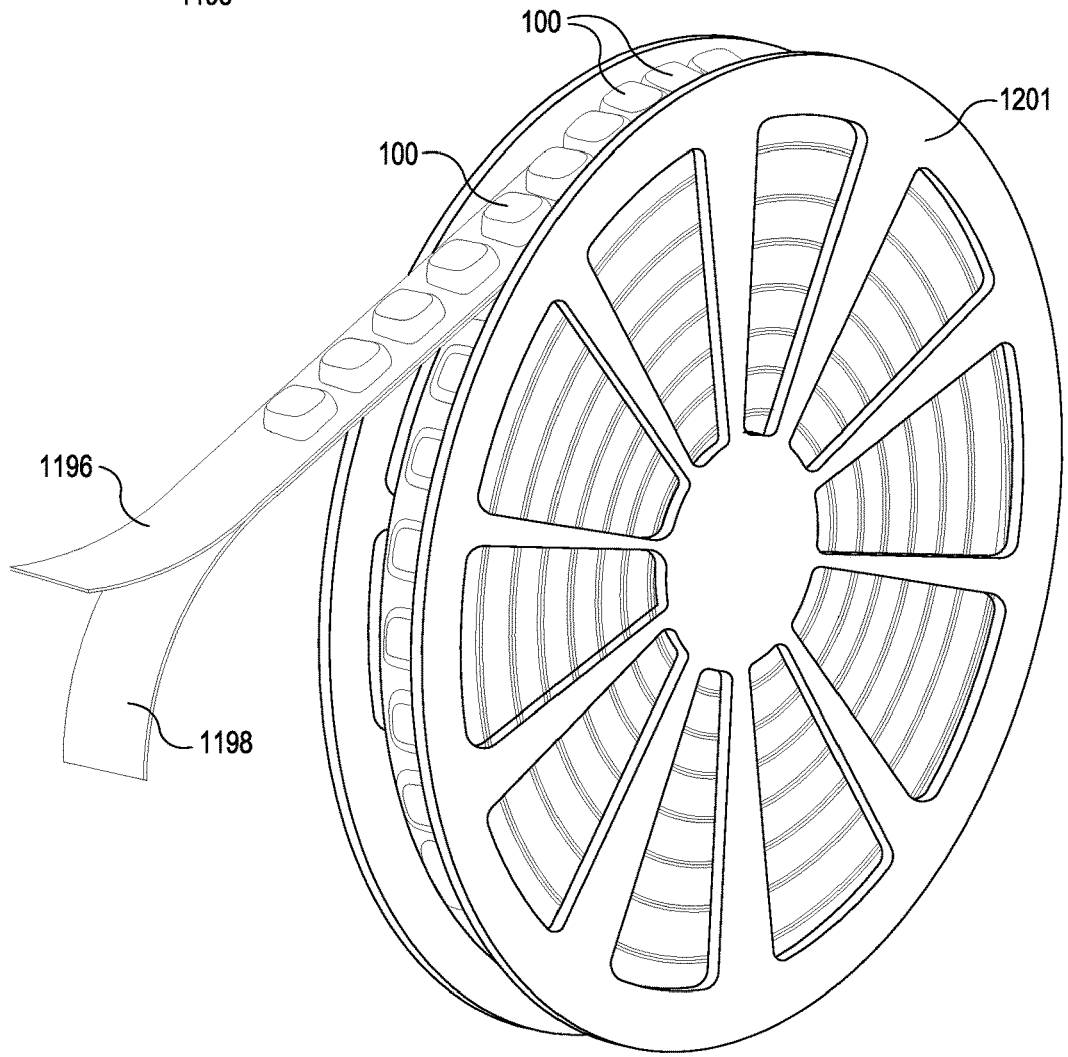
FIG. 12 illustrates a perspective view of an insect release system, according to at least one example.
Figure 13:
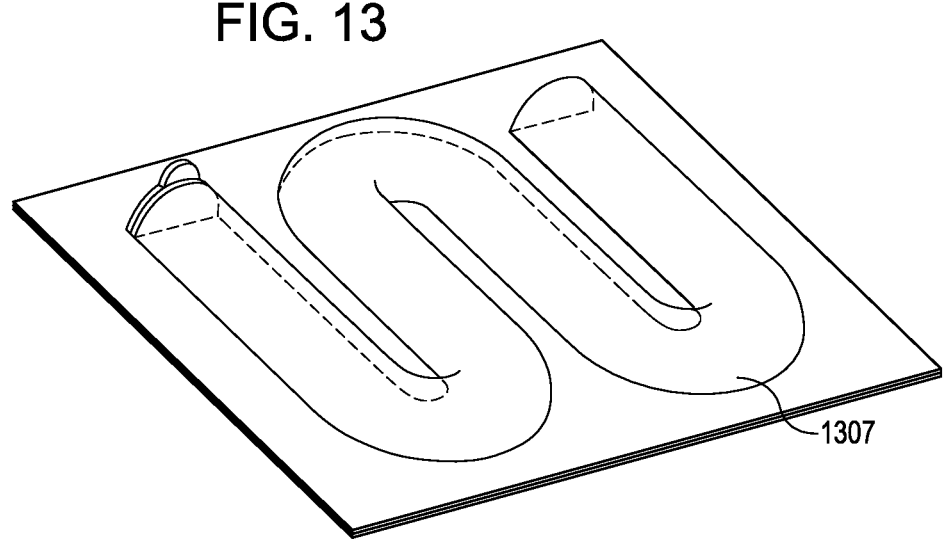
FIG. 13 illustrates a perspective view of an insect release system, according to at least one example.

FIG. 12 illustrates an embodiment of the insect release system 1194 that is embodied in a film strip on a reel 1201. The insect release system 1194 includes the bottom strip 1198 and the top strip 1196. In some examples, to release the insects from the insect storage and release devices 100, the reel 1201 is loaded into an insect release device and the top strip 1196 is fed to a second reel and the bottom strip is fed to a third reel. In this manner, as the second and third reels are turned, the top strip 1196 will be removed from the bottom strip 1198 thereby exposing the insects.

Figure 14A:
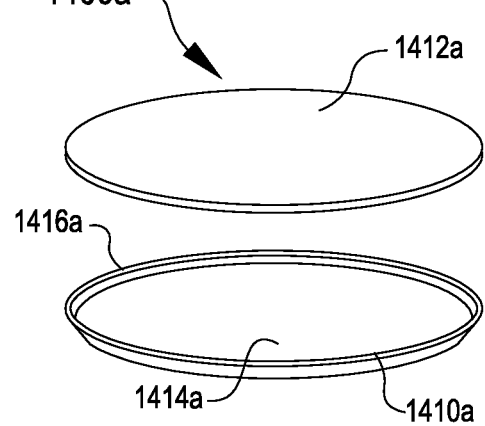
FIG. 14A illustrates a perspective view of an insect storage and release system, according to at least one example.
Figure 14B:
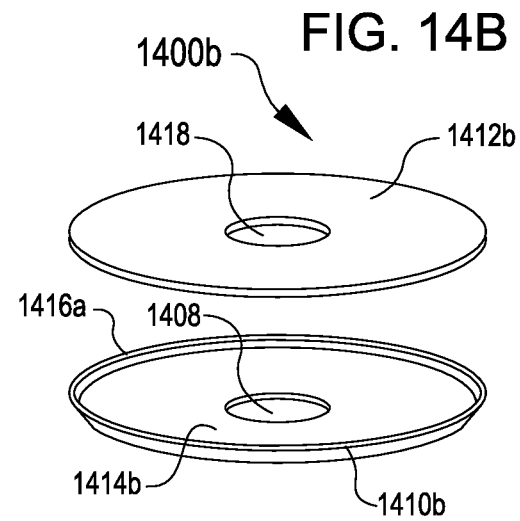
FIG. 14B illustrates a perspective view of an insect storage and release system, according to at least one example.

FIGS. 14A and 14B illustrate perspective views of insect storage and release systems 1400*a* and 1400*b*, according to at least one example. The insect storage and release systems 1400*a* and 1400*b* may be referred singularly as the insect storage and release system 1400. In some examples, a single insect storage and release system 1400 may constitute an insect storage and release system. The insect storage and release system 1400 may be configured to store insects in between planar layers of material. For example, a single layer of insects one-insect thick may be loaded into a bottom container of the insect storage and release system 1400. Next, a lid may be placed on top of the bottom container to enclose the insects within the bottom container. Another layer of insects may be formed on top of the earlier-formed layer in a similar manner (e.g., a bottom container filled with insects and enclosed with a lid). To release the insects, the lid may be removed from the respective bottom container to reveal the interior volume. The insect storage and release systems 1400 may enable dense storage, transportation, and release of insects such as adult mosquitoes.

Turning now to the details of the insect storage and release system 1400, the insect storage and release system 1400 includes a bottom container 1410 and a lid 1412. The bottom container 1410 includes a floor 1414 and a wall 1416 that encircles the wall 1416 to define an interior volume. The lid 1412 is sized to seal with a perimeter edge of the wall 1416 to enclose the interior volume of the bottom container 1410. When assembled, the lid 1412 may be brought towards the floor 1414 at least until a perimeter edge of the lid 1412 engages with the perimeter edge of the wall 1416 and/or interior surfaces of the wall 1416. The insect storage and release system 1400 may hold insects in a compressed state by pressing the lid 1412 against the bottom container 1410 to a predetermined pressure level while the insects are held in place between the lid and the bottom container. For example, the insects may be loaded in accordance with a packing pressure, as described herein. For example, the packing pressure may be measured given a force applied to the lid 1412 as it is brought into contact with the bottom container 1410 and a surface area of the bottom container 1412. In some examples, the packing pressure may be substantially between 0.5 PSI to 3 PSI. In some examples, the pressure may be lower than 0.5 PSI and may be higher than 3 PSI. In some examples, one or more pressure-maintaining items such as pneumatic cylinders or other resilient devices (e.g., spring) may be interposed between one or more layers of bottom containers 1410 and/or lids 1412 to maintain a constant compressive force between layers. The packing pressure may be used for packing insects in other insect storage and release systems described herein.

In some examples, combinations of bottom containers 1410 and lids 1412 may be stacked on top of each other to create a stacked arrangement of insect storage and release systems 1400. In some examples, the stacked arrangement of insect storage and release systems 1400 may be placed within a cylindrical tube or tube having a different cross section for bottom containers 1410 and lids 1412 having different cross sections (e.g., rectangular, etc.). The tube may function to retain the stacked insect storage and release systems 1400 and provide rigidity when the insect storage and release systems 1400 are transported. To release insects from one of the insect storage and release systems 1400, all insect storage and release systems 1400 within the tube (e.g., all "layers" of storage and release systems 1400) may be translated within the tube until a top insect storage and release system 1400 is adjacent a top opening of the tube. At this point, the lid 1412 of the top insect storage and release system 1400 may be removed and the insects within the corresponding bottom container 1410 may be free to exit the bottom container 1410 and/or the tube. Releasing insects from one bottom container 1410 may constitute a metered "dose" of insects, where a dose includes a quantity of insects from a discrete layer of the insect storage and release system (or from the entire system if only a single layer is employed). In some examples, the number of insects loaded into the bottom container 1410 may be metered such that each bottom container 1410 holds roughly the same quantity of insects. It should be appreciated that different sized doses of insects may be stored in different layers. For example, a first layer may include 100 insects, a second layer may include 50 insects, and a third layer may include 200 insects.

To store adult insects in the insect storage and release system 1400, the insects, such as mosquitoes, are first loaded into the bottom container 1410. This may include suppressing (e.g., sedating or otherwise reducing the energy level) the insects before placing them in the bottom container 1410. After the insects have been loaded into the bottom container 1410, the lid 1412 is releasably coupled with the wall 1416. In this manner, the insects may be retained within the volume bounded by the floor 1415, the wall 1416, and the lid 1412. In some examples, the lid 1412 may be releasably coupled with the wall 1416 using any suitable coupling such as a hook and loop fastener (e.g., Velcro® brand hook and loop fastener), adhesive, or other coupling disposed at the perimeter edges. To release insects from one layer (e.g., one bottom container 1410 and one lid 1412), the lid 1412 for that layer may be removed from the respective bottom container 1410 to reveal the interior volume. At this point, the insects may be free to fly from the bottom container 1410. In some examples, a blower, heater, and/or any other revival device may be arranged to encourage evacuation of the insects from the bottom container 1410.

In some examples, at least some bottom containers 1410 in a stack of insect storage and release systems 1400 may hold different quantities of insects. For example, a dosing requirement for a particular application may require a first insect quantity to be released on a first day, a second insect quantity to be released on a second day, and a third insect quantity to be released on a third day. Given this requirement, a stack of insect storage and release systems 1400 may be formed in which a top insect storage and release system 1400 may include the first insect quantity, a middle insect storage and release system 1400 may include the second insect quantity, and a bottom insect storage and release system 1400 may include the third insect quantity. The stack of insect storage and release systems 1400, whether in a tube or not, may be shipped with instructions for release. The instructions may inform a user that on a first day remove the lid 1412 of the top insect storage and release system 1400, on the second day remove the bottom container 1410 of the top insect storage and release system 1400 and the lid 1412 of the middle insect storage and release system 1400 and, and on the third day remove the bottom container 1410 of the middle insect storage and release system 1400 and the lid 1412 of the bottom insect storage and release system 1400.

Figure 15:
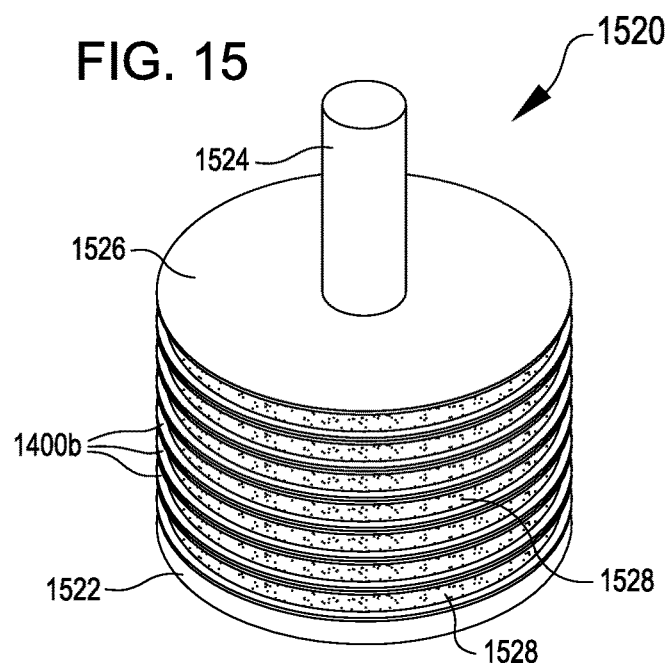
FIG. 15 illustrates a perspective view of a mounting structure for retaining the insect storage and release system of FIG. 14B, according to at least one example.

As illustrated, the insect storage and release systems 1400a and 1400b are structurally similar, with the exception that the insect storage and release system 1400b also includes a floor opening 1408 in the floor 1414b of the bottom container 1410b and a lid opening 1418 in the lid 1412b. As illustrated in FIG. 15, the floor opening 1408 and the lid opening 1418 may be sized to slide onto a mounting axle or other elongate member of a mounting structure 1520. For example, the mounting structure 1520 may include a bottom platform 1522 (e.g., a support foot) and an elongate cylindrical axle 1524 that extends vertically from the bottom platform 1522. The insect storage and release systems 1400b may be loaded onto the elongate cylindrical axle 1524 one by one, e.g., by placing a first bottom container 1410 on the elongate cylindrical axle 1524, loading insects into the first bottom container 1410, installing a first lid 1412, installing a second bottom container 1410, loading second insects into the second bottom container 1410, installing a second lid 1412, and repeating for subsequent layers. The bottom platform 1522 may function to support the insect storage and release systems 1400b and the axle 1524 may function to align the insect storage and release systems 1400b with each other. The diameter of the floor opening 1408 and the diameter of the lid opening 1418 may be sized to be slightly larger than an outside diameter of the elongate cylindrical axle 1524. In this manner, the insect storage and release systems 1400b may be slideably mounted on the axle 1524. The mounting structure 1520 may also include a removable lid 1526. The removable lid 1526 may be removed from the axle 1524 when the insect storage and release systems 1400 are being loaded and when insects are being released from an insect storage and release system 1400. In some examples, the mounting structure 1520 may be sized to be received by a cylindrical container.

The mounting structure 1520 is illustrated as including sections of foam 1528 (e.g., reticulated foam) arranged into layers. In this example, the mounting structure 1520 may be placed within a cylindrical container with the insects being placed between layers of the insect storage and release systems 1400 and the reticulated foam sections 1528. In some examples, the reticulated foam sections 1528 may be any other open cell foam, silicone, plastic, or other material capable of being compressed may be employed in place of the reticulated foam. The reticulated foam sections 1528 may occupy any excess volume within the interior volume and enable compression of the insects within the interior volume. The reticulated foam sections 1528 may be soaked in sugar water to provide food for insects within the interior volume.

The insect storage and release system 1400 has a cylindrical form factor (i.e., the bottom container 1410 and the lid 1412 have circular cross or ovoid sections), but other form factors such as rectangular, triangular, spherical, bulbous, and other shapes are also possible.

Figure 16:
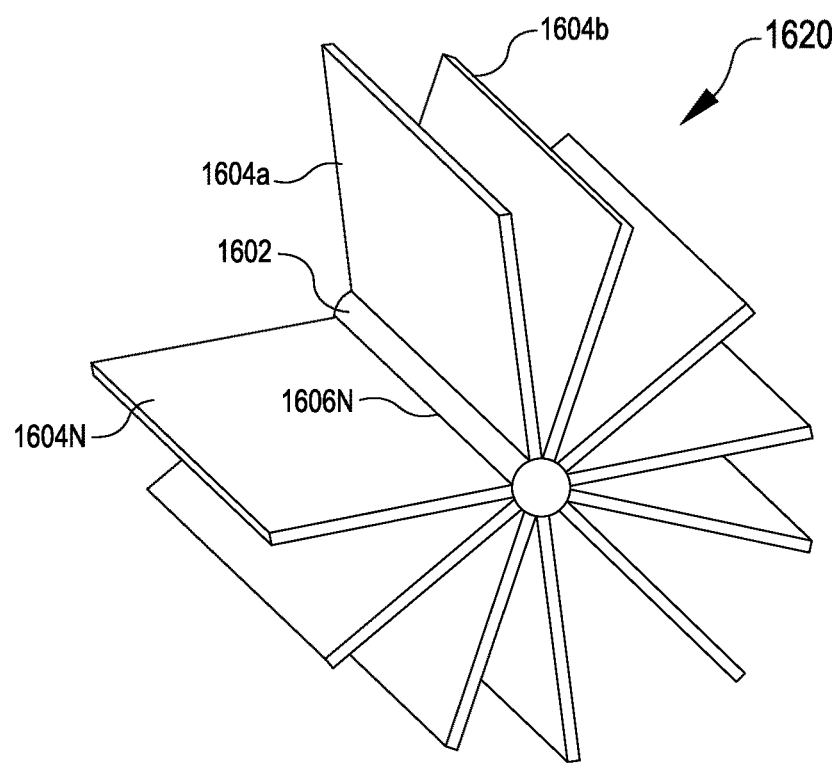
FIG. 16 illustrates a perspective view of an insect storage and release system, according to at least one example.

FIG. 16 illustrates a perspective view of an insect storage and release system 1600, according to at least one example. The insect storage and release system 1600 includes a central axle 1602 and a plurality of insect retaining structures 1604a-1604N extending radially from the central axle 1602. Each insect retaining structure 1604 is removably coupled to the central axle 1602 at a perimeter edge 1606. For example, the retaining structures 1604 may be coupled using an adhesive or hook and loop fasteners. In some examples, the central axle 1602 may include a plurality of slots into which perimeter edges 1606 of the retaining structures 1604 may be installed and securely held.

The retaining structures 1604 may include one or more sheets of planar material such as paper, plastic, metal, etc. In some examples, at least two retaining structures 1604a may form an insect storage and release subsystem by which insects may be stored. For example, the retaining structure 1604a may function as a containing layer of the subsystem to define an interior volume and may be used to retain a quantity of insects, and the retaining structure 1604b may function as a lid layer of the subsystem to define a lid for the containing layer. In this example, the retaining structure 1604a may also function as a lid layer of a subsystem that includes the retaining structure 1604N functioning as the containing layer.

In some examples, the retaining structures 1604 may function to retain other elements that are used to store insects. For example, structures similar to insect storage and release systems 1400 may be loaded in between the retaining structures 1604, and held in compression by the retaining structures 1604.

Depending on the application, the insects may be released from the insect storage and release system 1600 by separating the top and bottom retaining structures 1604 that are holding the insects. For example, in the illustrated system 1600, the insects held between the retaining structure 1604a and the retaining structure 1604N may be free for release.

Figure 17:
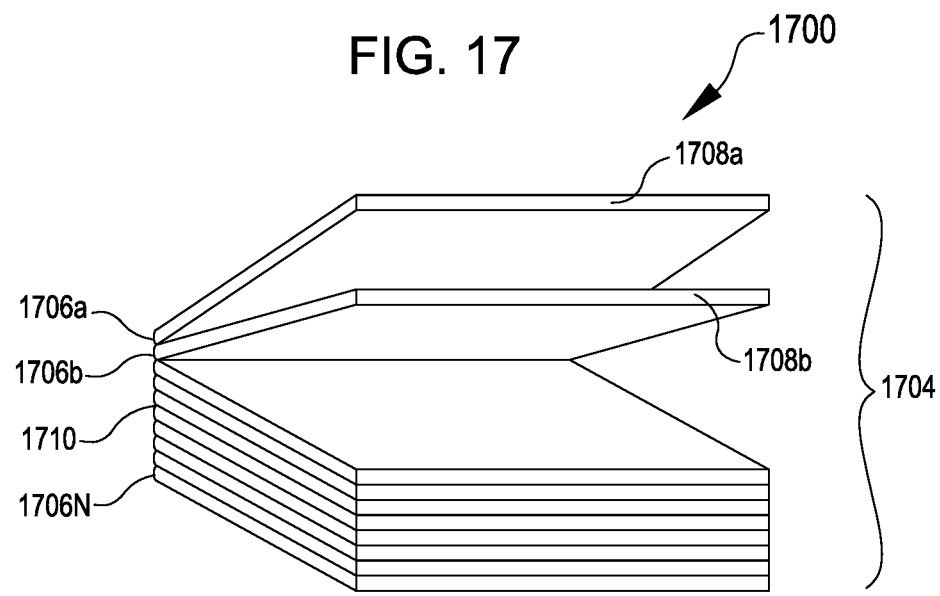
FIG. 17 illustrates a perspective view of an insect storage and release system, according to at least one example.

FIG. 17 illustrates a perspective view 1704 of an insect storage and release system 1700, according to at least one example. The insect storage and release system 1700 includes a plurality of storage layers 1706a-1706N stacked on top of each other. As labeled with respect to the storage layer 1706a, each storage layer 1706 includes a top planar section 1708a connected to a bottom planar section 1708b via a joint section 1710. The planar sections 1708 and joint section 1710 may be formed from the same material or from different materials. A stack of storage layers 1706 may be held within a storage container such as a box or other structure. In some examples, each storage layer 1706 may hold some predefined quantity of insects between the top planar section 1708a and the bottom planar section 1708b. To load insects, the top planar section 1708a may be folded back via the joint section 1710 to reveal an interior surface of the bottom planar section 1708b. In this orientation, the insects may be placed on the interior surface of the bottom planar section 1708b. Once a sufficient quantity of insects has been placed, the top planar section 1708a may be folded down and toward the bottom planar section 1708b. In this manner, the insects may be trapped and held between an interior surface of the top planar section 1708a and the interior surface of the top planar section 1708a. To release insects, the top planar section 1708a may be folded back again to reveal the interior surface of the bottom planar section 1708b. At this point, the insects may be free to fly from the interior surfaces of the planar sections 1708. In some examples, a blower, heater, and/or any other revival device may be arranged to encourage evacuation of the insects from the interior surface of the planar sections 1708.

Figure 18:
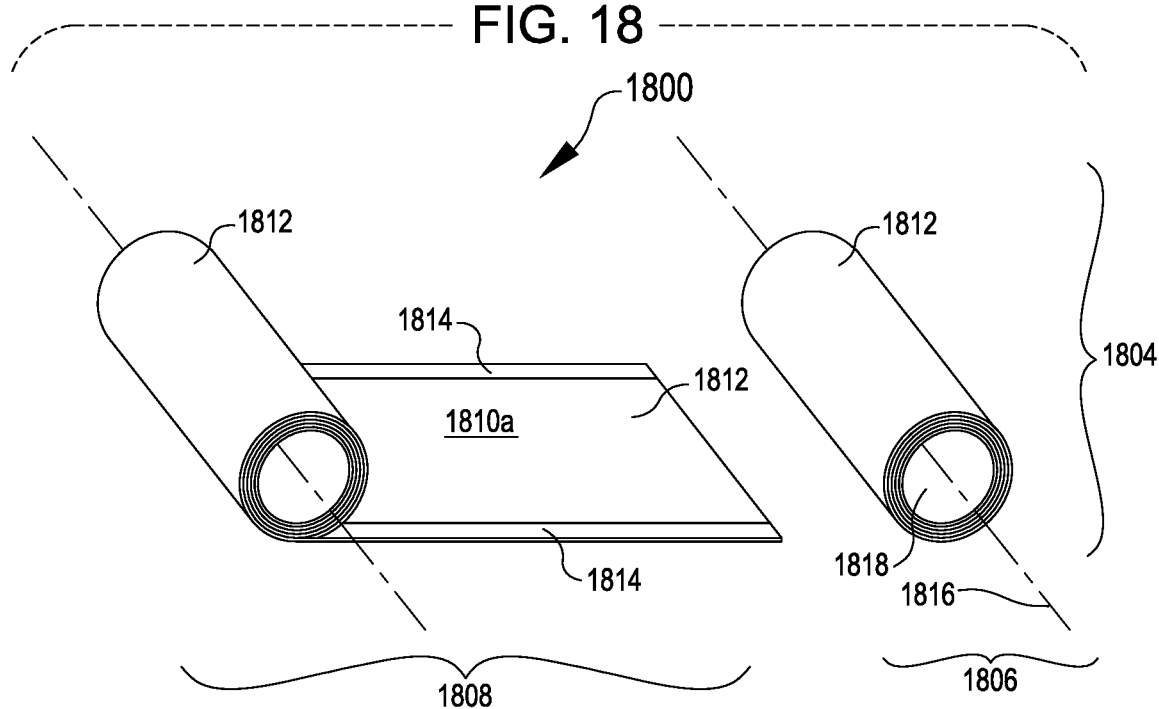
FIG. 18 illustrates perspective views of an insect storage and release system, according to at least one example.

FIG. 18 illustrates perspective views of an insect storage and release system 1800, according to at least one example. FIG. 18 also illustrates the insect storage and release system 1800 in a rolled state 1806 and a partially rolled state 1808 about a roll axis 1816. The insect storage and release system 1800 is formed from a single pliable mat 1812 that includes a first side 1810a and a second side opposite the first side. In some examples, the pliable mat 1812 is rolled around a mandrel 1818 or some other suitable cylindrical structure.

Generally, insects may be held between coaxial layers. For example, the pliable mat 1812 may be rolled out as in the partially rolled state 1808, and insects (e.g., in a sedated state) may be placed on the first side 1810a. Next, the pliable mat 1812 may be rolled about the roll axis 1816 such that the insects are held between the first side 1810a and the second side. In some examples, the pliable mat 1812 also includes an insect retaining material and/or coating disposed on at least the first side 1810a. For example, an open-cell foam may be provided on the first side 1810 to give the insects some place to roost or otherwise go when the pliable mat 1812 is rolled. To release insects, at least some portion of the pliable mat 1812 may be unrolled. In this manner at least some of the insects held between the layers may be exposed to the open air. At this point, the insects may be free to fly from the pliable mat 1812. In some examples, a blower, heater, and/or any other revival device may be arranged to encourage evacuation of the insects from the pliable mat 1812.

In some examples, the pliable mat 1812 also includes one or more retaining devices 1814. The retaining devices 1814, which may be located on one or both sides 1810 and/or as a separate device, are provided to retain the pliable mat 1812 in the rolled state 1808. For example, the retaining devices 1814 may include hook and loop fasteners (e.g., hooks on the first side 1810a and loops on the second side) that couple as the pliable mat 1812 is rolled about the roll axis 1816. The retaining devices 1814 may also be used to maintain a suitable compression force between layers of the roll. A tension for rolling the pliable mat 1812 may be computed based on a desired compression force between layers. The retaining devices 1814 may be configured to maintain this compression force by holding the layers.

Figure 19:
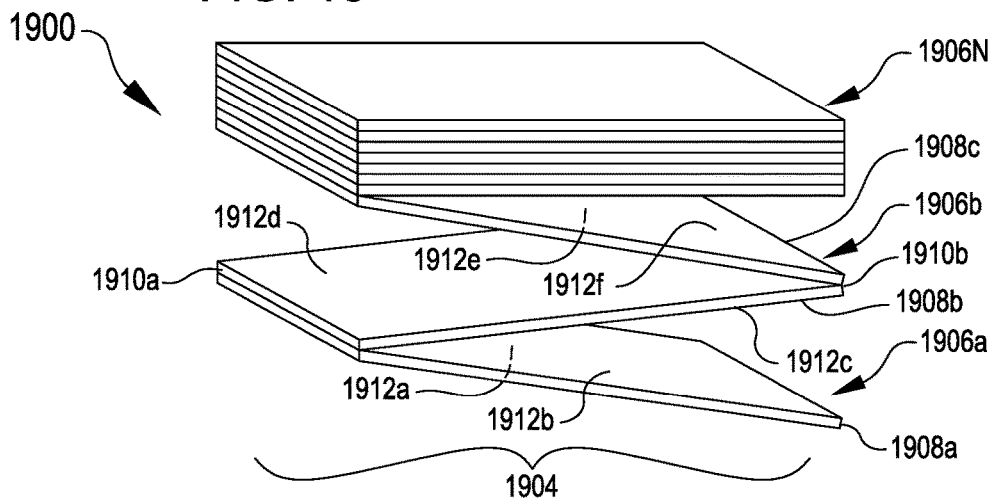
FIG. 19 illustrates a perspective view of an insect storage and release system, according to at least one example.

FIG. 19 illustrates a perspective view 1904 of an insect storage and release system 1900, according to at least one example. The insect storage and release system 1900 includes a plurality of storage layers 1906a-1906N stacked on top of each other and connected to each other via a joint section 1910. For example, as labeled with respect to the storage layer 1906a, the storage layer 1906a includes at least a planar section 1908a connected to a planar section 1908b via a joint section 1910a. The planar section 1908a includes a first surface 1912a and a second surface 1912b. Likewise, the planar section 1908b includes a third surface 1912c and a fourth surface 1912d. Likewise, the planar section 1908c includes a fifth surface 1912e and a sixth surface 1912f.

Insects may be loaded and held in between opposing top and bottom surfaces of the storage layers 1906. For example, the insects may be loaded and held between the second surface 1912b of the planar section 1908a and the third surface of the 1912c of the planar section 1908b. Other insects may be held between the fourth surface 1912d and the fifth surface 1912e. In this manner, the insects are held and retained in between opposing surfaces of the Z shape. Thus, in at least one example, the insect storage and release system 1900 includes a single layer 1906 that includes a structure that is comparable in shape and design to the layers of the insect storage and release device 1706. In the system 1900, however, each layer may be connected via additional joint sections 1910 to make one uniform Z folding structure. To release insects, the planar sections 1908 may be separated from each other. At this point, the insects may be free to fly out of the V-shaped structure. In some examples, a blower, heater, and/or any other revival device may be arranged to encourage evacuation of the insects from the surfaces of the layers 1906.

The system 1900 may also include retaining devices configured to maintain compression within the stack of layers. For example, rubber bands, straps, tension clips, or the like may be used to hold the layers in compression.

Figure 20:
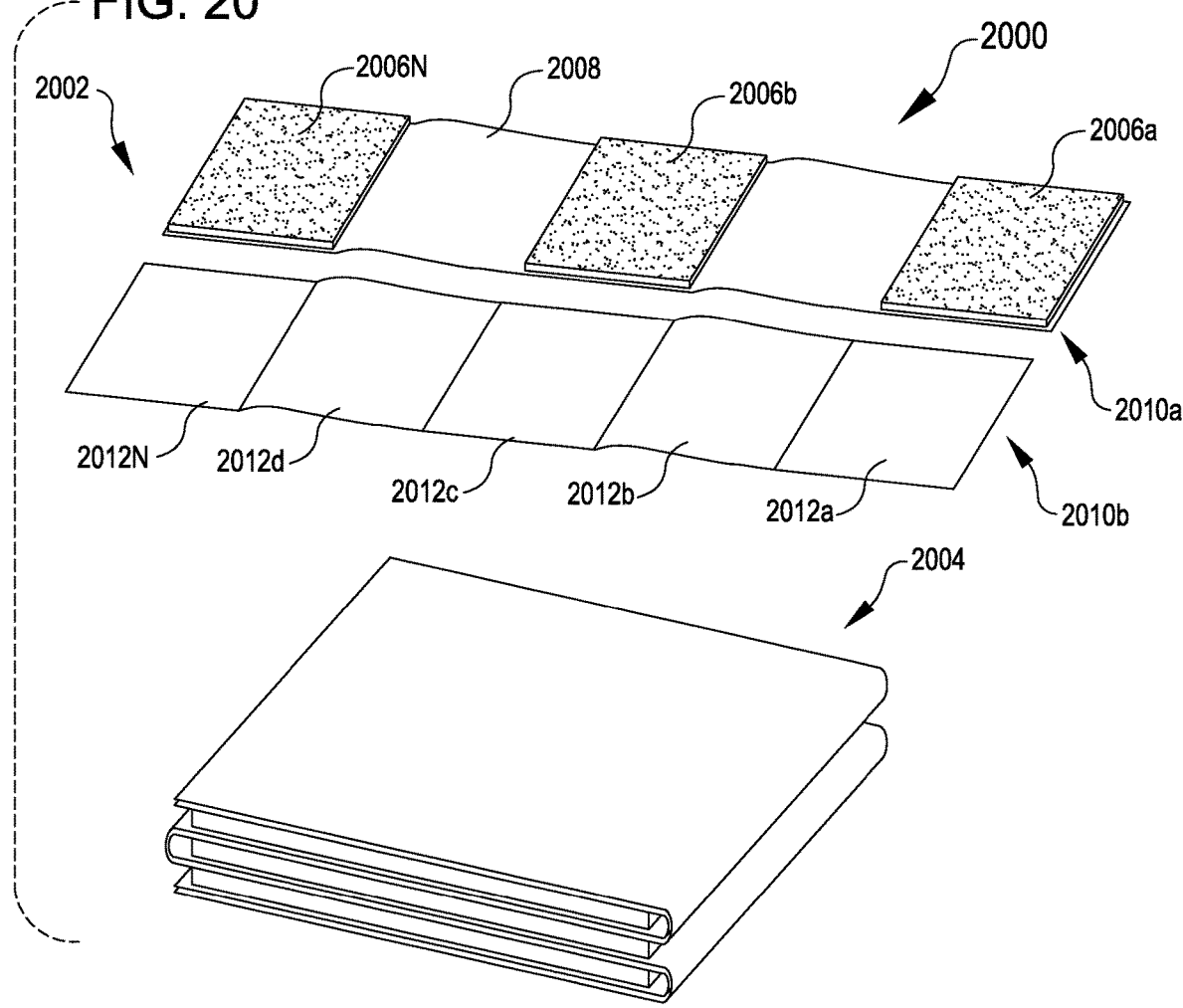
FIG. 20 illustrates perspective views of an insect storage and release system, according to at least one example.

FIG. 20 illustrates perspective views 2002 and 2004 of an insect storage and release system 2000, according to at least one example. In perspective view 2002, a top side 2010a and a bottom side 2010b of the insect storage and release system 2000 are illustrated in an expanded state. In the perspective view 2004, the insect storage and release system 2000 is illustrated in a stacked state.

The insect storage and release system 2000 includes at least two insect retaining sections 2006a-2006N connected to a pliable mat 2008 (e.g., at the top side 2010a). In this example, the pliable mat 2008 is formed from a rectangular piece of thin paper and is divided into a plurality of mat sections 2012a-2012N. The insect retaining sections 2006 may be formed from a foam. The insect retaining sections 2006 may be spaced roughly equally apart from each other on the pliable mat 2008, with the space between being about equal to a width of a single insect retaining section 2006 (e.g., a mat section 2012). In the expanded state illustrated in the first perspective view 2002 with the top side 2010a facing up, the insects may be placed on the insect retaining section 2006a. After which, the mat section 2012b may be folded onto the insect retaining section 2006a to provide a barrier between the insect retaining section 2006a and the insect retaining section 2006b. The similar approach can be taken for loading insects in the insect retaining section 2006b. Once all layers have been loaded, the insect storage and release system 2000 will take the form of the stacked state in perspective view 2004. To release the insects held within an insect retaining section 2006, the mat section 2012 that is on top of the insect retaining section 2006 may be removed to reveal the insects to the open air. At this point, the insects may be free to fly off of the insect retaining section 2006. In some examples, a blower, heater, and/or any other revival device may be arranged to encourage evacuation of the insects from the surfaces of the insect retaining sections 2006.

The system 2000 may also include retaining devices configured to maintain compression within the stack of layers. For example, rubber bands, straps, tension clips, or the like may be used to hold the layers in compression.

The illustrated insect storage and release systems described herein may be formed from a thermoformable plastic, foil, paper, compostable products, rubbers, silicone/urethane, foam, 3D printed resin and filament, insect food (e.g., sucrose, bread, etc.). In some examples, the material used may be color coded to signify a characteristic such as volume of the container or quantity of insects held therein. The material may also be tinted (e.g., tinted plastic), UV protected (e.g., UV protected plastic), and have color-changing properties. The insect storage and release system described herein may also be loaded with food (e.g., sugar water, sugar capsule, etc.).

In some examples, the insect storage and release systems described herein are loaded directly from an insect sortation system. The insect sortation system may be configured to singulate and sort insects based on predefined characteristic (e.g., sex, species, size, etc.). Once singulated, the insects can be blown, driven, or otherwise loaded into the insect storage and release systems from a singulation pathway of the insect sortation system. In some examples, insects from the singulation pathway are loaded into a holding chamber, and the insects are loaded from the holding chamber into the insect storage and release systems.

In some examples, the insect storage and release devices may include climate or other environmental control such as temperature, humidity, and/or pressure control. Such control may be maintained during storage, packing, shipping, transportation, etc. In some examples, the insect storage and release devices may be compatible for feeding of insects. In some examples, the insect storage and release devices may include a tracking mechanism such as radio-frequency identification (RFID) tracking. In some examples, the insect storage and release devices may enable timed release such as a maze form factor (e.g., designed such that it takes an insect some predefined amount of time to exit), barrier (e.g., food barrier that is eaten by insects), or dissolvable. For example, FIG. 14 illustrates an example release maze 1407, according to at least one example. In some examples, the insects of the insect storage and release devices may be dispersed using any suitable dispersion technique including, for example, hanging, shooting, dropping from air, floating, within plants, or via the mail (e.g., mailed to a person's home and released by the person). In some examples, the insect storage and release devices may include automatic dispersion features including, for example, hole patterns, tabs, or multi-material for automated opening. In some examples, the insect storage and release devices may be capable of use by existing insect release methods that utilize blower release, drone release, room temperature release, any of which may be paired with revival techniques (e.g., warming, providing oxygen, etc.).

Releasing the insects from the insect storage and release devices described herein may be performed in any suitable manner, which may include, for example, placing the insects onto a recovery plate (e.g., a foam mat) and allowing the insects to recover on the plate, placing the insects onto a tray below an airstream. As the insects fly up into the airstream the insects will get blown out of the release device.

Figure 21:
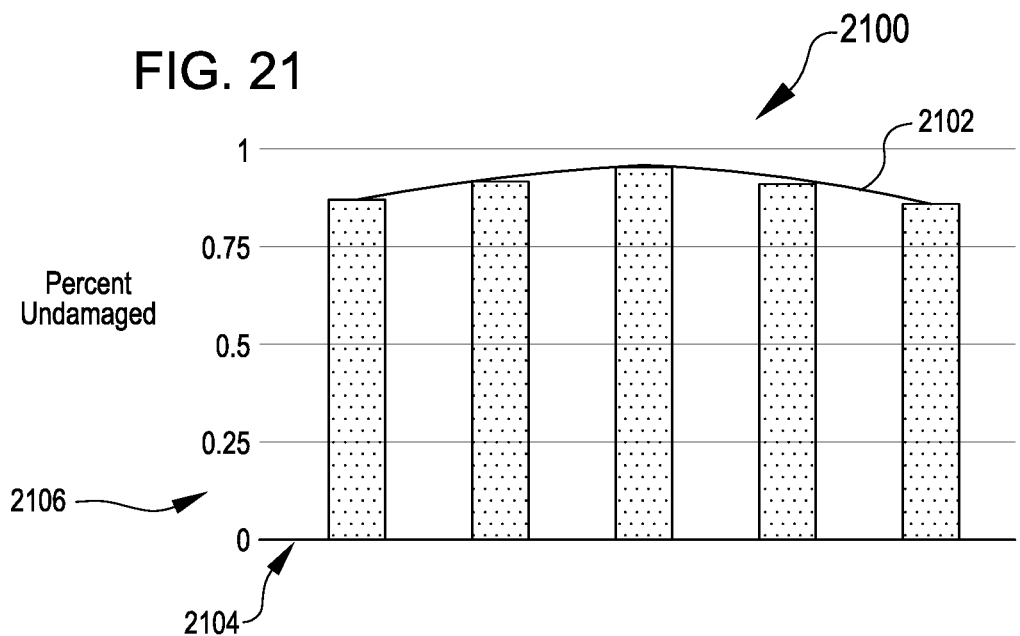
FIG. 21 illustrates a graph depicting an insect packing curve, according to at least one example.

FIG. 21 illustrates a graph 2100 depicting an insect packing curve 2102, according to at least one example. In some examples, loading insects into an insect storage and release device may be performed with respect to the insect packing curve 2102. The insect packing curve 2102 may define that for a given volume, a first quantity of insects will not harm each other, a second larger quantity of insects for the same volume will hurt each and should be avoided (e.g., because they will fly around and bump into each other), and a third larger quantity of insects for the same volume will not hurt each other (e.g., because the insects are packed to closely to fly around and hurt each other). In some examples, a similar curve represents compressed insects.

The insect packing curve 2102 represents a packing curve for compressed insects. In particular, the graph 2100 illustrates the number of mosquitoes packed per cubic center along the X axis 2104 (increasing in number of insects from a lowest quantity on the far left to a highest quantity on the far right) and the percentage of male mosquitoes undamaged along the Y axis 2106. In this example, when the density is around 200 male mosquitoes per cubic centimeter, the lowest percentage of those insects is damaged.

Figure 22:
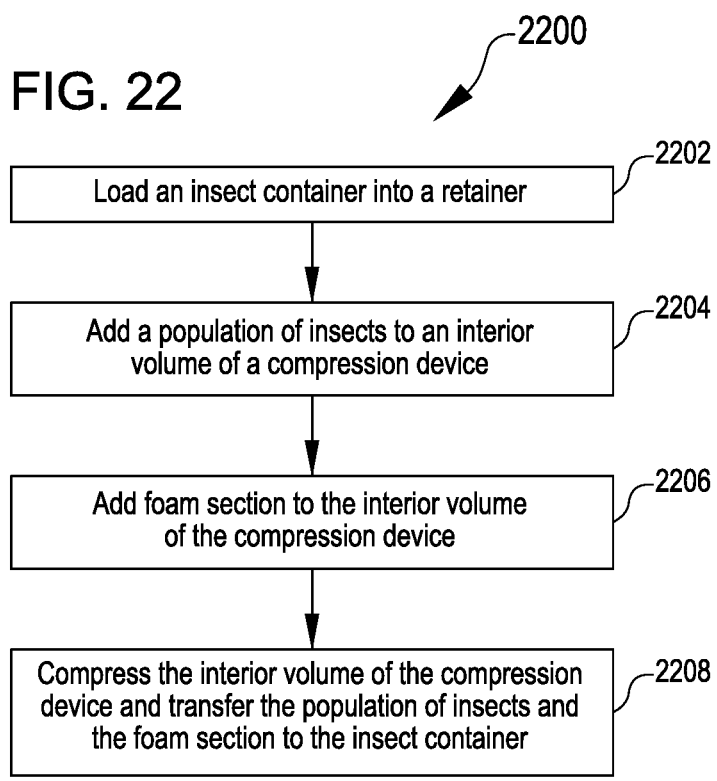
FIG. 22 illustrates a flow chart showing a process for compressing insects into a fixed volume, according to at least one example.

FIG. 22 illustrates a flow chart showing a process 2200 for compressing insects into a fixed volume such as the interior volume 110 of the insect storage and release device 100, according to at least one example. The process 2200 begins at block 2202 by loading an insect container into a retainer. For example, the insect storage and release device 100 may be loaded into the retainer block 532.

At block 2204, the process 2200 includes adding a population of insects to an interior volume of a compression device (e.g., the compression apparatus 534). For example, this may include loading insects into the chamber 542. In some examples, the compression device includes a syringe held within a mounting bracket that aligns with and is releasably coupled to the retainer. In this example, the interior volume may be defined within a barrel of the syringe.

At block 2206, the process 2200 includes adding a foam section to the interior volume of the compression device. For example, this may include adding the foam section 212 into the chamber 542. Depending on which end of the compression device is loaded with insects, the block 2204 may be performed before or after the block 2206.

At block 2208, the process 2200 includes compressing the interior volume of the compression device and transferring the population of insects and the foam section to the insect container. This may include applying a force to the plunger 546 of the compression apparatus 534 to cause the plunger to translate within the interior volume and transfer the insects into the insect container.

In some examples, the block 2208 includes compressing the interior volume at least until a predefined packing pressure of the interior volume is reached. In this example, the process 2200 may further include adding a pressure-maintaining item to the interior volume such that a first portion of the pressure-maintaining item contacts the foam section, and adding a lid to the insect container to enclose the interior volume such that a second portion of the pressure-maintaining item contacts an interior portion of the lid. The pressure-maintaining item may be configured to maintain the predefined packing pressure of the interior volume by asserting opposing forces on the foam section and the lid. The pressure-maintaining item may include at least one a spring or a constant force material.

In some examples, the process 2200 may further include suppressing the population of insects at a particular temperature. For example, the population of insects may be chilled at a particular temperature (e.g., between 9 degrees C. and 14 degrees C.) to reduce their activity. In some examples, at least one of blocks 2204-2208 is performed at the particular temperature.

In some examples, the process 2200 may further include maintaining at least one environmental condition of the interior volume at least while performing the block 2208. The environmental condition may include at least one of humidity or pressure.

Example 1

In this example, there is provided an insect storage and release system, including:
a container including a floor and a wall that encircles the floor to define an interior volume, the interior volume sized to receive a plurality of adult insects;
a lid sized and configured to releasably couple with the wall to enclose the interior volume; and
a sealing structure to releasably couple the wall and the lid and securely retain insects within the interior volume.

Example 2

In this example, there is provided an insect storage and release system, including:
an axle to receive insect retaining structures; and
a plurality of insect retaining structures that are removably mountable on the axle, wherein each insect retaining structure includes:
a containing layer that defines an interior volume, the interior volume sized to receive a plurality of adult insects; and
a lid layer that indexes with the container layer to enclose the interior volume, wherein insects are retained within the interior volume when the lid layer is indexed with the containing layer.

Example 3

In this example, there is provided a system of any of the preceding or subsequent examples, wherein an opening is defined in each of the plurality of insect retaining structures, and the axle receives each of the plurality of insect retaining structures via each respective opening to retain the respective insect retaining structure.

Example 4

In this example, there is provided a system of any of the preceding or subsequent examples, wherein each of the plurality of insect retaining structures is removably mounted on the axle via a perimeter edge of the respective insect retaining structure.

Example 5

In this example, there is provided an insect retaining structure, including:
a first planar section including a first surface and a second surface opposite the first surface;
a second planar section including a third surface and a fourth surface opposite the third surface; and
a joint section that connects a first perimeter edge of the first planar section and a second perimeter edges of the second planar section,
wherein the first planar section is foldable along the joint section such that the first surface of the first planar section selectively contacts the third surface of the second planar section, and wherein insects are retained between the first surface and the third surface when the first surface is in contact with the third surface.

Example 6

In this example, there is provided an insect retaining structure, including:
a pliable mat including a first surface on a first side and a second surface on a second side; and
a retaining device,
wherein the pliable mat retains insects between the first surface and the second surface when the pliable mat is rolled about a roll axis, wherein the retaining device retains the pliable mat in a rolled state.

Example 7

In this example, there is provided an insect retaining structure, including:
a pliable mat including a first side and a second side opposite the first side, the pliable map defining a plurality of portions;
a first insect retaining section including a third side and a fourth side, the fourth side of the first insect retaining section connected to the pliable mat on the first side of the pliable mat at a first portion of the plurality of portions; and a second insect retaining section including a fifth side and a sixth side, the sixth side of the second insect retaining section connected to the pliable mat on the first side of the pliable mat at a second portion of the plurality of portions, the second portion separate from the first portion by a third portion, wherein the pliable mat is foldable such that first side of the third portion overlays the fourth side of the first insect retaining section and the second side of the second portion overlays the first side of the third portion.

Example 8

In this example, there is provided an insect storage and release device, including:
a bottom;
a top flange;
a perimeter wall that connects the bottom and the top flange, wherein the perimeter wall and the bottom form a cylinder that defines a cylindrical interior volume for receiving a population of insects, and wherein an opening is formed in the top flange;
a population of insects disposed within the interior volume; and
a lid sized and configured to enclose the opening and prevent the population of insects from exiting the cylinder.

Example 8

In this example, there is provided an insect storage and release device of any of the preceding or subsequent examples, wherein one or more perforations are formed in at least one of the bottom, the perimeter wall, or the lid.

Example 9

In this example, there is provided an insect storage and release device of any of the preceding or subsequent examples, wherein the lid includes an adhesive ring configured to adhere the lid to a surface of the top flange.

Example 10

In this example, there is provided an insect storage and release device of any of the preceding or subsequent examples, wherein the lid includes:
a lid bottom; and
at least one lid wall connected to and extending from the lid bottom.

Example 11

In this example, there is provided an insect storage and release device of any of the preceding or subsequent examples, wherein a cross-sectional area of the opening is larger than a second cross-sectional area of the lid bottom.

Example 12

In this example, there is provided an insect storage and release device of any of the preceding or subsequent examples, wherein the lid is configured to enclose the opening by an interference fit between the perimeter wall and the at least one lid wall.

Example 13

In this example, there is provided an insect storage and release device of any of the preceding or subsequent examples, wherein: the lid further includes a lid flange that is connected to and extends around the at least one lid wall, and the insect storage and release device further includes a tab that connects the top flange and the lid flange.

Example 14

In this example, there is provided an insect storage and release device of any of the preceding or subsequent examples, wherein the opening is sized to receive a foam section and wherein the foam section includes an insect food.

Example 15

In this example, there is provided an insect storage and release device of any of the preceding or subsequent examples, wherein the lid is formed from a foam section.

Example 16

In this example, there is provided an insect storage and release device of any of the preceding or subsequent examples, wherein the population of insects includes a compressed population of insects.

Example 17

In this example, there is provided an insect storage and release device of any of the preceding or subsequent examples, wherein the compressed population of insects is compressed to a density of between substantially 100 and 300 insects per milliliter.

Example 18

In this example, there is provided an insect storage and release device of any of the preceding or subsequent examples, wherein the bottom is bulbous or planar.

Example 19

In this example, there is provided an insect storage and release device of any of the preceding or subsequent examples, further including a detent mechanism including a first feature connected to the lid and a second feature connected to the perimeter wall, the second feature configured to arrest rotation of the lid relative to the perimeter wall.

Example 20

In this example, there is provided a system including:
a bottom section including a plurality of insect sections, each insect section including an insect compartment, each insect compartment including at least one live insect; and
a lid that extends over and encloses each insect compartment, wherein the lid is configured for individual access to each insect compartment.

Example 21

In this example, there is provided a system of any of the preceding or subsequent examples, wherein the bottom section includes a plurality of perforation lines that extend between the plurality of insect sections, the plurality of perforation lines are configured for individual separation of each insect section from other insect sections of the plurality of insect sections.

Example 22

In this example, there is provided a system of any of the preceding or subsequent examples, wherein the lid or the bottom section that forms the insect compartments includes one or more perforations that enable air flow between the insect compartments and outside the insect compartments.

Example 23

In this example, there is provided a system of any of the preceding or subsequent examples, wherein each insect compartment includes a portion of insect food.

Example 24

In this example, there is provided a system of any of the preceding or subsequent examples, wherein the plurality of insect sections is arranged in a 1×N array, N is more than one.

Example 25

In this example, there is provided a system of any of the preceding or subsequent examples, wherein the plurality of insect sections is arranged in an M×N array, where M is more than one and N is more than one.

Example 26

In this example, there is provided a system of any of the preceding or subsequent examples, wherein each insect compartment is sized and configured to receive a compressed population of live insects.

Example 27

In this example, there is provided a system of any of the preceding or subsequent examples, wherein the bottom section includes a sheet of flexible material and the plurality of insect sections is formed as deformations in the sheet of flexible material.

Example 28

In this example, there is provided a system of any of the preceding or subsequent examples, wherein the bottom section includes a microplate and the lid includes a plurality of flexible protrusions configured to enclose the insect compartments by partially extending into the insect compartments.

Example 29

In this example, there is provided a system of any of the preceding or subsequent examples, further including an insect release device configured to selectively separate portions of the lid from corresponding bottom sections to expose interior volumes of the insect sections.

Example 30

In this example, there is provided a method of compressing insects, including:
loading an insect container into a retainer;
adding a population of insects to an interior volume of a compression device;
adding a foam section to the interior volume of the compression device; and
compressing the interior volume of the compression device and transferring the population of insects and the foam section to the insect container.

Example 31

In this example, there is provided a method of any of the preceding or subsequent examples, further including cooling the population of insects at a predetermined temperature.

Example 32

In this example, there is provided a method of any of the preceding or subsequent examples, wherein at least one of loading the insect container, adding the population of insects, adding the foam section, or compressing the interior volume is performed at a predetermined temperature.

Example 33

In this example, there is provided a method of any of the preceding or subsequent examples, wherein the compression device includes a syringe held within a mounting bracket that aligns with and is releasably coupled to the retainer.

Example 34

In this example, there is provided a method of any of the preceding or subsequent examples, wherein the interior volume is defined within a barrel of the syringe.

Example 35

In this example, there is provided a method of any of the preceding or subsequent examples, wherein compressing the interior volume includes translating a plunger of the syringe through the barrel toward a distal tip of the barrel to transfer the population of insects into the insect container.

Example 36

In this example, there is provided a method of any of the preceding or subsequent examples, further including maintaining at least one environmental condition of the interior volume at least while compressing the interior volume of the compression device, the environmental condition including at least one of humidity or air pressure.

Example 37

In this example, there is provided a method of any of the preceding or subsequent examples, wherein compressing the interior volume includes compressing the interior volume at least until a predefined packing pressure of the population of insects within the interior volume is reached.

Example 38

In this example, there is provided a method of any of the preceding or subsequent examples, further including:
adding a pressure-maintaining item to the interior volume such that a first portion of the pressure-maintaining item contacts the foam section; and
adding a lid to the insect container to enclose the interior volume such that a second portion of the pressure-maintaining item contacts an interior portion of the lid, wherein the pressure-maintaining item is configured to maintain the predefined packing pressure of the interior volume by asserting opposing forces on the foam section and the lid.

The method of claim 39, wherein the pressure-maintaining item includes at least one a variable force spring or a constant force spring.

Example 40

In this example, there is provided an insect rearing device, including:
a pouch in which is formed a pocket;
a first duct connected to a first side of the pocket and extending in a first direction, the first duct configured to retain an aqueous solution, larvae insect food, and one or more insect larvae; and
a second duct connected to a second side of the pocket and extending in a second direction, the second duct configured to retain adult insect food.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An insect storage and release device, comprising:
   a bottom;
   a top flange;
   a perimeter wall that connects the bottom and the top flange, wherein the perimeter wall and the bottom form a cylinder that defines a cylindrical interior volume for receiving insects, and wherein an opening is formed in the top flange;
   a population of insects disposed within the interior volume;
   a lid comprising an adhesive ring, wherein the lid is sized and configured to:
      enclose the opening via adhesion between the adhesive ring and the top flange; and
      prevent the population of insects from exiting the cylinder; and
   a foam section disposed within the cylindrical interior volume and in physical contact with the lid and a portion of the population of insects, wherein the foam section is configured to maintain a compressive force on the population of insects.

2. The insect storage and release device of claim 1, wherein one or more perforations are formed in the lid.

3. The insect storage and release device of claim 1, wherein the opening is sized to receive the foam section and wherein the foam section comprises an insect food.

4. The insect storage and release device of claim 1, wherein the lid is formed from the foam section.

5. The insect storage and release device of claim 1, wherein the population of insects comprises a compressed population of insects.

6. The insect storage and release device of claim 5, wherein the compressed population of insects is compressed to a density of between substantially 100 and 300 insects per milliliter.

7. The insect storage and release device of claim 1, wherein the bottom is bulbous or planar.

8. The insect storage and release device of claim 1, further comprising a detent mechanism comprising a first feature connected to the lid and a second feature connected to the perimeter wall, the second feature configured to arrest rotation of the lid relative to the perimeter wall.

9. The insect storage and release device of claim 1, wherein the lid is formed from the foam section, wherein the foam section is configured to enable airflow between the interior volume and outside the interior volume.

10. The insect storage and release device of claim 9, wherein the foam section comprises a first section that extends into the interior volume and a second section that extends along the top flange.

11. The insect storage and release device of claim 10, wherein the first section comprises a cylindrical section and the second section comprises a rectangular section.

12. The insect storage and release device of claim 1, wherein the lid comprises an insect food.

* * * * *